(12) United States Patent
Mayse et al.

(10) Patent No.: US 12,721,677 B2
(45) **Date of Patent: *Sep. 1, 2026**

(54) APPARATUSES AND METHODS FOR INJURING NERVE TISSUE

(71) Applicant: Nuvaira, Inc., Minneapolis, MN (US)

(72) Inventors: Martin L. Mayse, Wayzata, MN (US); Mark E. Deem, Mountain View, CA (US)

(73) Assignee: Nuvaira, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/392,637

(22) Filed: Dec. 21, 2023

(65) Prior Publication Data

US 2024/0122643 A1 Apr. 18, 2024

Related U.S. Application Data

(63) Continuation of application No. 16/243,781, filed on Jan. 9, 2019, now Pat. No. 11,849,994, which is a (Continued)

(51) Int. Cl.

*A61B 18/14* (2006.01)
*A61B 18/00* (2006.01)

(52) U.S. Cl.

CPC .................... *A61B 18/1492* (2013.01); *A61B 2018/00023* (2013.01); *A61B 2018/0022* (2013.01);

(Continued)

(58) Field of Classification Search

CPC ..... A61B 18/08; A61B 18/14; A61B 18/1492; A61B 2018/1475; A61B 2018/00482; A61B 2018/00505; A61B 2018/00559; A61B 2018/00345; A61B 2018/00386; A61B 2018/00404; A61B 2018/00279; A61B 2018/00285; A61B 2018/00023; A61B 2018/0022; A61B 2018/00267;

(Continued)

(56) References Cited

U.S. PATENT DOCUMENTS 5,722,403 A 3/1998 David
5,902,268 A 5/1999 Saab (Continued)

FOREIGN PATENT DOCUMENTS

WO WO-00/51510 9/2000
WO WO-2009/137819 11/2009

(Continued)

OTHER PUBLICATIONS

Application and File history for U.S. Appl. No. 12/463,304, filed May 8, 2009. Inventors: Mayse et al.

(Continued)

*Primary Examiner* — Thomas A Giuliani

(74) *Attorney, Agent, or Firm* — Merchant & Gould P.C.

(57) ABSTRACT

Systems, delivery devices, and methods to treat to ablate, damage, or otherwise affect tissue. The treatment systems are capable of delivering energy to nerve tissue in a target region such that at least a portion of the nerve tissue is replaced by scar tissue or otherwise altered to inhibit reinnervation in the target region.

19 Claims, 20 Drawing Sheets

Related U.S. Application Data continuation of application No. 14/349,599, filed as application No. PCT/US2012/058485 on Oct. 2, 2012, now Pat. No. 10,201,386.

(60) Provisional application No. 61/543,759, filed on Oct. 5, 2011.

(52) U.S. Cl.
CPC ............... *A61B 2018/00226* (2013.01); *A61B 2018/00232* (2013.01); *A61B 2018/00285* (2013.01); *A61B 2018/00434* (2013.01); *A61B 2018/00541* (2013.01)

(58) Field of Classification Search
CPC .......... A61B 2018/00226; A61B 2018/00232; A61B 2018/00434; A61B 2018/00541; A61B 2018/00214
USPC ...... 606/34, 40–42, 49, 50; 607/98, 99, 101, 607/113, 115, 116
See application file for complete search history.

(56) References Cited

U.S. PATENT DOCUMENTS

| | | | | |
|---|---|---|---|---|
| 6,012,457 | A | 1/2000 | Lesh | |
| 6,210,355 | B1 | 4/2001 | Edwards et al. | |
| 6,322,559 | B1 | 11/2001 | Daulton et al. | |
| 6,411,852 | B1 | 6/2002 | Danek et al. | |
| 6,451,013 | B1 | 9/2002 | Bays et al. | |
| 6,634,363 | B1 | 10/2003 | Danek et al. | |
| 7,027,869 | B2 | 4/2006 | Danek et al. | |
| 7,608,275 | B2 | 10/2009 | Deem et al. | |
| 7,770,584 | B2 | 8/2010 | Danek et al. | |
| 8,088,127 | B2 | 1/2012 | Mayse et al. | |
| 8,133,497 | B2 | 3/2012 | Deem et al. | |
| 8,172,827 | B2 | 5/2012 | Deem et al. | |
| 8,226,638 | B2 | 7/2012 | Mayse et al. | |
| 8,338,164 | B2 | 12/2012 | Deem et al. | |
| 8,483,831 | B1 | 7/2013 | Hlavka | |
| 8,489,192 | B1 | 7/2013 | Hlavka | |
| 8,660,647 | B2 | 2/2014 | Pamis et al. | |
| 8,731,672 | B2 | 5/2014 | Hlavka | |
| 8,740,895 | B2 | 6/2014 | Mayse et al. | |
| 8,777,943 | B2 | 7/2014 | Mayse et al. | |
| 8,808,280 | B2 | 8/2014 | Mayse et al. | |
| 8,821,489 | B2 | 9/2014 | Mayse et al. | |
| 8,911,439 | B2 | 12/2014 | Mayse et al. | |
| 8,932,289 | B2 | 1/2015 | Mayse et al. | |
| 8,961,391 | B2 | 2/2015 | Deem et al. | |
| 8,961,507 | B2 | 2/2015 | Mayse et al. | |
| 8,961,508 | B2 | 2/2015 | Mayse et al. | |
| 9,005,195 | B2 | 4/2015 | Mayse | |
| 9,017,324 | B2 | 4/2015 | Mayse et al. | |
| 9,125,643 | B2 | 9/2015 | Hlavka et al. | |
| 9,149,328 | B2 | 10/2015 | Dimmer et al. | |
| 9,339,618 | B2 | 5/2016 | Deem et al. | |
| 9,398,933 | B2 | 7/2016 | Mayse | |
| 9,498,283 | B2 | 11/2016 | Deem et al. | |
| 9,539,048 | B2 | 1/2017 | Hlavka et al. | |
| 9,649,153 | B2 | 5/2017 | Mayse et al. | |
| 9,649,154 | B2 | 5/2017 | Mayse et al. | |
| 9,662,171 | B2 | 5/2017 | Dimmer et al. | |
| 9,668,809 | B2 | 6/2017 | Mayse et al. | |
| 9,675,412 | B2 | 6/2017 | Mayse et al. | |
| 9,867,986 | B2 | 1/2018 | Hlavka et al. | |
| 10,201,386 | B2 * | 2/2019 | Mayse | A61B 18/1492 |
| 11,849,994 | B2 * | 12/2023 | Mayse | A61B 18/1492 |
| 2002/0087208 | A1 | 7/2002 | Koblish et al. | |
| 2002/0115991 | A1 | 8/2002 | Edwards | |
| 2003/0159700 | A1 | 8/2003 | Laufer et al. | |
| 2003/0233099 | A1 | 12/2003 | Danaek et al. | |
| 2004/0226556 | A1 | 11/2004 | Deem et al. | |
| 2006/0225742 | A1 | 10/2006 | Deem et al. | |
| 2006/0254600 | A1 | 11/2006 | Danek et al. | |
| 2007/0100390 | A1 | 5/2007 | Danaek et al. | |
| 2007/0129720 | A1 | 6/2007 | Demarais et al. | |
| 2007/0156185 | A1 | 7/2007 | Swanson et al. | |
| 2008/0097424 | A1 | 4/2008 | Wizeman | |
| 2009/0043301 | A1 | 2/2009 | Jarrard et al. | |
| 2009/0069797 | A1 * | 3/2009 | Danek | A61N 1/06 606/33 |
| 2009/0112203 | A1 | 4/2009 | Danek | |
| 2009/0131928 | A1 | 5/2009 | Edwards et al. | |
| 2009/0306644 | A1 * | 12/2009 | Mayse | A61B 18/24 128/898 |
| 2011/0118725 | A1 | 5/2011 | Mayse et al. | |
| 2011/0152855 | A1 | 6/2011 | Mayse et al. | |
| 2011/0178569 | A1 | 7/2011 | Parnis et al. | |
| 2011/0257523 | A1 * | 10/2011 | Hastings | A61B 18/0206 601/2 |
| 2011/0257647 | A1 | 10/2011 | Mayse et al. | |
| 2011/0301587 | A1 | 12/2011 | Deem et al. | |
| 2012/0016358 | A1 | 1/2012 | Mayse et al. | |
| 2012/0016364 | A1 | 1/2012 | Mayse et al. | |
| 2012/0172680 | A1 * | 7/2012 | Gelfand | A61N 1/36114 606/41 |
| 2012/0203216 | A1 | 8/2012 | Mayse et al. | |
| 2012/0203222 | A1 | 8/2012 | Mayse et al. | |
| 2012/0209261 | A1 | 8/2012 | Mayse et al. | |
| 2012/0209296 | A1 | 8/2012 | Mayse et al. | |
| 2012/0221087 | A1 | 8/2012 | Parnis et al. | |
| 2012/0253336 | A1 | 10/2012 | Littrup | |
| 2012/0302909 | A1 | 11/2012 | Mayse et al. | |
| 2012/0310233 | A1 | 12/2012 | Dimmer | |
| 2012/0316552 | A1 | 12/2012 | Mayse et al. | |
| 2013/0310822 | A1 | 11/2013 | Mayse et al. | |
| 2014/0025063 | A1 | 1/2014 | Kaplan et al. | |
| 2014/0276792 | A1 | 9/2014 | Kaveckis et al. | |
| 2014/0316398 | A1 | 10/2014 | Kelly | |
| 2014/0358136 | A1 | 12/2014 | Kelly | |
| 2014/0371809 | A1 | 12/2014 | Parnis et al. | |
| 2015/0126986 | A1 | 5/2015 | Kelly | |
| 2015/0141985 | A1 | 5/2015 | Mayse et al. | |
| 2016/0022351 | A1 | 1/2016 | Kaveckis et al. | |
| 2016/0038725 | A1 | 2/2016 | Mayse et al. | |
| 2016/0220851 | A1 | 8/2016 | Mavse et al. | |
| 2016/0278845 | A1 | 9/2016 | Mavse | |
| 2016/0310210 | A1 | 10/2016 | Harshman et al. | |
| 2017/0014571 | A1 | 1/2017 | Deem et al. | |
| 2017/0050008 | A1 | 2/2017 | Mayse | |
| 2017/0072176 | A1 | 3/2017 | Deem et al. | |
| 2017/0143421 | A1 | 5/2017 | Mayse et al. | |
| 2017/0245911 | A1 | 8/2017 | Mayse et al. | |
| 2018/0028748 | A1 | 2/2018 | Deem et al. | |

FOREIGN PATENT DOCUMENTS

| | | |
|---|---|---|
| WO | WO-2011/056684 | 5/2011 |
| WO | WO-2011/060200 | 5/2011 |
| WO | WO-2011/127216 | 10/2011 |

OTHER PUBLICATIONS

Application and File history for U.S. Appl. No. 13/245,522, filed Sep. 26, 2011. Inventors: Mayse et al.

Application and File history for U.S. Appl. No. 13/452,660, filed Apr. 20, 2012. Inventors: Mayse et al.

Application and File history for U.S. Appl. No. 13/452,664, filed Apr. 20, 2012. Inventors: Mayse et al.

Application and File history for U.S. Appl. No. 13/523,223, filed Jun. 14, 2012. Inventors: Hlavka et al.

Application and File history for U.S. Appl. No. 13/920,801, filed Jun. 18, 2013. Inventors: Hlavka et al.

PCT International Preliminary Report on Patentability corresponding to PCT/US2012/058485, dated Apr. 8, 2014.

PCT Written Opinion of the International Searching Authority PCT/US2012/058485, dated Dec. 17, 2012.

(56) References Cited

OTHER PUBLICATIONS

PCT Search Report of the International Searching Authority PCT/US2012/058485, dated Dec. 17, 2012.

* cited by examiner

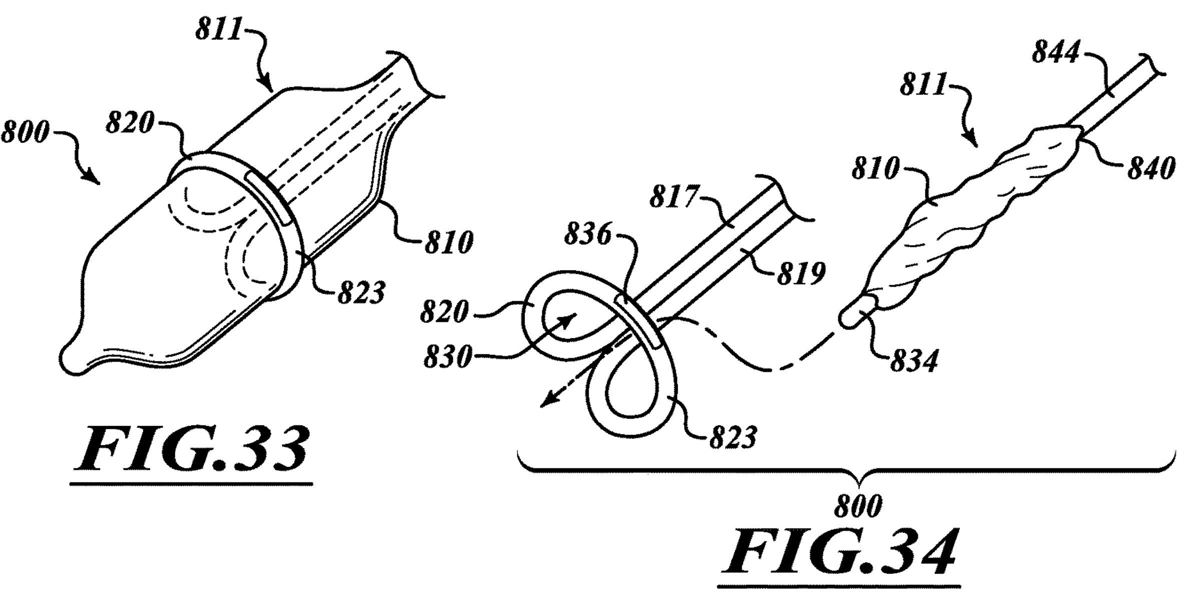
811
800
820
810
823
FIG.33
844
811
840
810
817
836
819
820
830
834
823
800
FIG.34
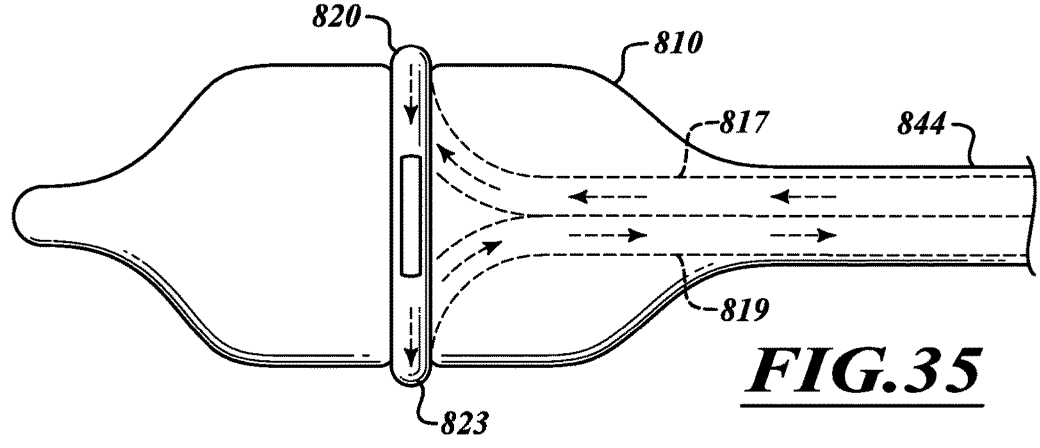
820
810
817
844
819
823
FIG.35
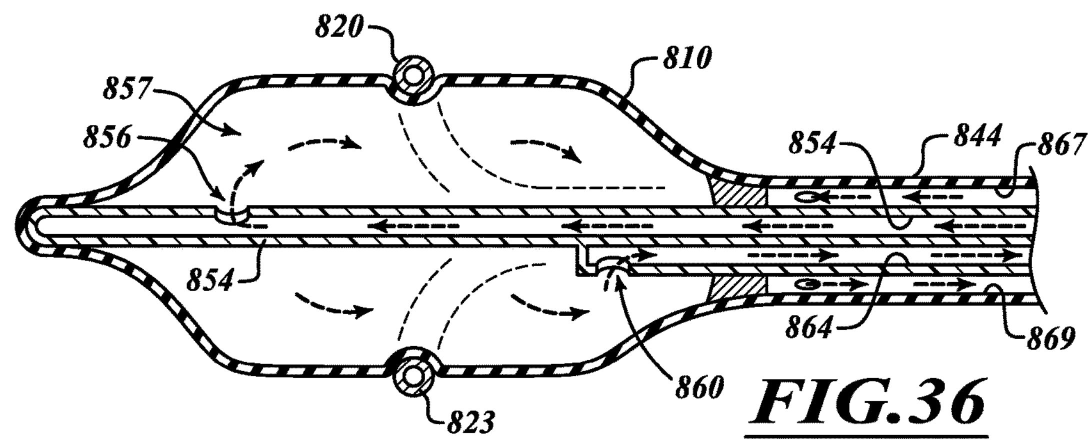
820
810
857
856
854
844
867
854
864
869
860
823
FIG.36

APPARATUSES AND METHODS FOR INJURING NERVE TISSUE

RELATED APPLICATIONS

This application is a continuation of application Ser. No. 16/243,781, filed Jan. 9, 2019, now U.S. Pat. No. 11,849, 994, which is a continuation of application Ser. No. 14/349, 599 filed Apr. 3, 2014, now U.S. Pat. No. 10,201,386 which is a National Phase entry of PCT Application No. PCT/US2012/058485 filed Oct. 2, 2012, which claims priority the benefit of U.S. Application No. 61/543,759 filed Oct. 5, 2011, each of which is hereby fully incorporated herein by reference.

BACKGROUND

Technical Field

The present invention generally relates to systems, apparatuses, and methods for altering tissue, and more particularly, the invention relates to apparatuses or treatment systems for injuring nerve tissue.

Description of the Related Art

Pulmonary diseases may cause a wide range of problems that adversely affect performance of the lungs. Pulmonary diseases, such as asthma and chronic obstructive pulmonary disease ("COPD"), may lead to increased airflow resistance in the lungs. Mortality, health-related costs, and the size of the population having adverse effects due to pulmonary diseases are all substantial. These diseases often adversely affect quality of life. Symptoms are varied but often include cough; breathlessness; and wheeze. In COPD, for example, breathlessness may be noticed when performing somewhat strenuous activities, such as running, jogging, brisk walking, etc. As the disease progresses, breathlessness may be noticed when performing non-strenuous activities, such as walking. Over time, symptoms of COPD may occur with less and less effort until they are present all of the time, thereby severely limiting a person's ability to accomplish normal tasks.

Pulmonary diseases are often characterized by airway obstruction associated with blockage of an airway lumen, thickening of an airway wall, alteration of structures within or around the airway wall, or combinations thereof. Airway obstruction can significantly decrease the amount of gas exchanged in the lungs, resulting in breathlessness. Blockage of an airway lumen can be caused by excessive intraluminal mucus or edema fluid, or both. Thickening of the airway wall may be attributable to excessive contraction of the airway smooth muscle, airway smooth muscle hypertrophy, mucous glands hypertrophy, inflammation, edema, or combinations thereof. Alteration of structures around the airway, such as destruction of the lung tissue itself, can lead to a loss of radial traction on the airway wall and subsequent narrowing of the airway.

Asthma can be characterized by contraction of airway smooth muscle, smooth muscle hypertrophy, excessive mucus production, mucous gland hypertrophy, and/or inflammation and swelling of airways. These abnormalities are the result of a complex interplay of local inflammatory cytokines (chemicals released locally by immune cells located in or near the airway wall), inhaled irritants (e.g., cold air, smoke, allergens, or other chemicals), systemic hormones (chemicals in the blood such as the anti-inflammatory cortisol and the stimulant epinephrine), local nervous system input (nerve cells contained completely within the airway wall that can produce local reflex stimulation of smooth muscle cells and mucous glands), and the central nervous system input (nervous system signals from the brain to smooth muscle cells and mucous glands carried through the vagus nerve). These conditions often cause widespread temporary tissue alterations and initially reversible airflow obstruction that may ultimately lead to permanent tissue alteration and permanent airflow obstruction that make it difficult for the asthma sufferer to breathe. Asthma can further include acute episodes or attacks of additional airway narrowing via contraction of hyper-responsive airway smooth muscle that significantly increases airflow resistance. Asthma symptoms include recurrent episodes of breathlessness (e.g., shortness of breath or dyspnea), wheezing, chest tightness, and cough.

Emphysema is a type of COPD often characterized by the alteration of lung tissue surrounding or adjacent to the airways in the lungs. Emphysema can involve destruction of lung tissue (e.g., alveoli tissue such as the alveolar sacs) that leads to reduced gas exchange and reduced radial traction applied to the airway wall by the surrounding lung tissue. The destruction of alveoli tissue leaves areas of emphysematous lung with overly large airspaces that are devoid of alveolar walls and alveolar capillaries and are thereby ineffective at gas exchange. Air becomes "trapped" in these larger airspaces. This "trapped" air may cause over-inflation of the lung, and in the confines of the chest restricts the in-flow of oxygen rich air and the proper function of healthier tissue. This results in significant breathlessness and may lead to low oxygen levels and high carbon dioxide levels in the blood. This type of lung tissue destruction occurs as part of the normal aging process, even in healthy individuals. Unfortunately, exposure to chemicals or other substances (e.g., tobacco smoke) may significantly accelerate the rate of tissue damage or destruction. Breathlessness may be further increased by airway obstruction. The reduction of radial traction may cause the airway walls to become "floppy" such that the airway walls partially or fully collapse during exhalation. An individual with emphysema may be unable to deliver air out of their lungs due to this airway collapse and airway obstructions during exhalation.

Chronic bronchitis is a type of COPD that can be characterized by contraction of the airway smooth muscle, smooth muscle hypertrophy, excessive mucus production, mucous gland hypertrophy, and inflammation of airway walls. Like asthma, these abnormalities are the result of a complex interplay of local inflammatory cytokines, inhaled irritants, systemic hormones, local nervous system, and the central nervous system. Unlike asthma where respiratory obstruction may be largely reversible, the airway obstruction in chronic bronchitis is primarily chronic and permanent. It is often difficult for a chronic bronchitis sufferer to breathe because of chronic symptoms of shortness of breath, wheezing, and chest tightness, as well as a mucus producing cough.

Different techniques can be used to assess the severity and progression of pulmonary diseases. For example, pulmonary function tests, exercise capacity, and quality of life questionnaires are often used to evaluate subjects. Pulmonary function tests involve objective and reproducible measures of basic physiologic lung parameters, such as total airflow, lung volume, and gas exchange. Indices of pulmonary function tests used for the assessment of obstructive pulmonary diseases include the forced expiratory volume in 1 second (FEV1), the forced vital capacity (FVC), the ratio of the FEV1 to FVC, the total lung capacity (TLC), airway resistance and the testing of arterial blood gases. The FEV1 is the volume of air a patient can exhale during the first second of a forceful exhalation which starts with the lungs completely filled with air. The FEV1 is also the average flow that occurs during the first second of a forceful exhalation. This parameter may be used to evaluate and determine the presence and impact of any airway obstruction. The FVC is the total volume of air a patient can exhale during a forceful exhalation that starts with the lungs completely filled with air. The FEV1/FVC is the fraction of all the air that can be exhaled during a forceful exhalation during the first second. A FEV1/FVC ratio less than 0.7 after the administration of at least one bronchodilator defines the presence of COPD. The TLC is the total amount of air within the lungs when the lungs are completely filled and may increase when air becomes trapped within the lungs of patients with obstructive lung disease. Airway resistance is defined as the pressure gradient between the alveoli and the mouth to the rate of air flow between the alveoli and the mouth. Similarly, resistance of a given airway would be defined as the ratio of the pressure gradient across the given airway to the flow through the airway. Arterial blood gases tests measure the amount of oxygen and the amount of carbon dioxide in the blood and are the most direct method for assessing the ability of the lungs and respiratory system to bring oxygen from the air into the blood and to get carbon dioxide from the blood out of the body.

Exercise capacity tests are objective and reproducible measures of a patient's ability to perform activities. A six-minute walk test (6 MWT) is an exercise capacity test in which a patient walks as far as possible over a flat surface in 6 minutes. Another exercise capacity test involves measuring the maximum exercise capacity of a patient. For example, a physician can measure the amount of power the patient can produce while on a cycle ergometer. The patient can breathe 30 percent oxygen and the work load can increase by 5-10 watts every 3 minutes.

Quality of life questionnaires assess a patient's overall health and well-being. The St. George's Respiratory Questionnaire is a quality of life questionnaire that includes 75 questions designed to measure the impact of obstructive lung disease on overall health, daily life, and perceived well-being. The efficacy of a treatment for pulmonary diseases can be evaluated using pulmonary function tests, exercise capacity tests, and/or questionnaires. A treatment program can be modified based on the results from these tests and/or questionnaires.

BRIEF SUMMARY

In some embodiments, a treatment system can be navigated through vessels to damage tissue. The vessels can be airways, such as the right and left main bronchi of the lung root, as well as more distal airways within the lungs, to damage tissue to treat a wide range of pulmonary symptoms, conditions, and/or diseases, including, without limitation, asthma, COPD, obstructive lung diseases, or other diseases that lead to, for example, an increased resistance to airflow in the lungs. Nerve tissue located along a bronchial tree can be injured to attenuate transmission of nervous system signals to distal regions of the lung to dilate airways to enhance lung function. The injury can inhibit reinnervation that would impair lung function by allowing nervous system signals to cause contraction of the smooth muscle. Thus, the region of the lung can be denervated for an extended length of time. In some procedures, the injury results in permanent denervation because scar tissue prevents reinnervation. In some embodiments, treatment systems can be configured to target tissue next to large vessels (e.g., the trachea) or tissue next to relatively small vessels (e.g., blood vessels), as well as other types of hollow vessels. The treatment system can also be used in other parts of the body.

Some embodiments are directed to systems for injuring nerve tissue. The severity of injury can be selected to prevent undesirable regrowth of nerve tissue. Nerve trunks (e.g., nerve trunks along an airway of a lung, nerve trunks along a trachea, etc.), nerve fibers, or other types of nerve tissue can be damaged to attenuate nervous system signals to, for example, inhibit constriction of smooth muscles in distal airways or elicit another desired response. In some embodiments, a scar may form to inhibit reinnervation of nerve tissue, thereby preventing an unwanted amount of functional recovery for a desired period of time. To inhibit reinnervation of a target region, axons, myelin, endoneurium, or other structures can be targeted.

By way of example, if all of the axons along a section of a nerve trunk are destroyed, distal airways can dilate to reduce airway resistance in distal regions of the lung. Scar tissue can prevent regrowth of the damaged axons. Compressive forces (e.g., forces from a compression ring), therapeutic agents (e.g., toxins), or combinations thereof can further prevent or control nerve regrowth.

In some embodiments, a method of treating a subject comprises positioning an energy delivery device in a passageway in the subject. The energy delivery device delivers energy to nerve tissue in a target region along a vessel such that at least a portion of the nerve tissue is replaced by scar tissue which inhibits reinnervation in the target region. In certain embodiments, the vessel is an airway of a lung, trachea, or esophagus.

In some embodiments, an energy delivery system includes an intraluminal energy delivery apparatus configured to be positioned in a passageway of a bronchial tree. The energy delivery apparatus includes an energy emitter configured to deliver energy to nerve tissue in a target region to create sufficient scar tissue in place of the nerve tissue to inhibit reinnervation in the target region.

An energy delivery system, in some embodiments, includes a power source and an intraluminal energy delivery apparatus configured for delivery along a lumen of a vessel. The delivery apparatus includes an energy emitter coupled to the power source. A controller is configured to control the amount of energy delivered from the power source to the energy emitter such that the energy emitter outputs energy to damage nerve tissue located along the airway to produce one or more lesions containing sufficient scar tissue in place of the nerve tissue to inhibit reinnervation in the one or more lesions.

A method of treating a subject, in some embodiments, includes positioning an energy delivery device in a passageway in a subject. To treat the respiratory system, a therapeutically effective amount of energy can injure tissue to affect lung function for a desired length of time (e.g., 1 month, 3 months, 6 months, 10 months, 1 year, 2 years, 3 years, or other length of time). In some embodiments, a lesion is formed along a nerve trunk. The lesion can include scar tissue that inhibits, limits, or substantially prevents transmission of nervous system signals to the lung. The scar tissue can replace nerve tissue. In some procedures, the lesion can have a first end positioned in a first intracartilaginous space and a second end positioned in a second intracartilaginous space. To minimize unwanted damage, the lesion can generally extend about a cartilage ring in the wall of the airway. Most of the cartilage ring can remain undamaged to avoid or minimize stenosis. Any number of lesions can be formed along a single nerve trunk. Lesions can overlap such that an overlapping region has a relatively high density for enhanced retardation of nerve regrowth. A physician can select a type of injury based on, for example, Sunderland nerve injury classification. For example, the injury can be a type 3 injury or higher.

In some embodiments, a method of treating a subject includes intraluminally delivering energy to a nerve trunk or other nerve tissue positioned along an airway. If the airway is in or proximate to a lung, the injury causes a decrease in airway resistance of a distal portion of the lung. The injury can also substantially prevent reinnervation of the nerve tissue to keep the airway resistance of a distal portion of the lung at or below a threshold airway resistance for a desired period of time. In other procedures, energy is delivered to nerve tissue along the trachea. The nerve tissue can be part of a nerve trunk along the trachea, part of the vagus nerve, or other nerve tissue to which energy can be delivered energy from the trachea. The delivered injury can include injuring substantially all axons of a nerve fascicle, myelin sheaths, and the endoneuriums of the fascicles to prevent nervous system signals from passing beyond the treatment site. Some or all of the nerve trunks along a section of an airway can be injured to ensure that nervous system signals are not transmitted distally. If the nerve tissue is along a bronchiole, the energy can be delivered to nerve fibers within an airway wall.

In some embodiments, an intraluminal apparatus is configured to be positioned in a lumen of an airway. The apparatus includes an energy emitter capable of delivering energy to a target region to produce at least one lesion that alters respiratory function of a region of the lung distal to the lesion for a desired period of time. In some embodiments, a power source is coupled to the energy emitter. A controller is configured to control the amount of energy delivered from the power source to the energy emitter in order to damage nerve tissue located along the airway. The damaged tissue can alter respiratory function of distal regions of the lung.

At least some embodiments of inhibiting reinnervation includes, without limitation, sufficiently injuring nerve tissue to inhibit regrowth of nerve tissue (including destroying or ablating nerve tissue), causing the formation of non-nerve tissue which blocks or attenuates nervous system signals, applying forces (e.g., compressive forces), replacing nerve tissue with another tissue (e.g., non-nerve tissue), or combinations thereof by using ablation elements or assemblies, electrodes, needles (e.g., needles for injecting a scarring agent), compression rings, cooling balloons, implants, and/or combinations thereof. The nerve tissue can include, without limitation, parasympathetic afferent nerves, parasympathetic efferent nerves, myelinated nerves, unmyelinated nerves, individual nerve fibers, and/or c-fiber nerves.

In some embodiments, power, total dose, time of energy delivery, and efficiency can be adjusted to obtain desired lesions. In electrode embodiments, electrode(s) can have long length to create long lesions. The length of the lesion can minimize the chance of reinnervation. Multiple sites can be targeted and the electrodes can be operated in monopolar mode, bipolar mode, or the like. The delivery of energy can be ramped, constant, or varied and be part of a repeated treatment (e.g., bursts of applied energy separated by seconds, minutes, days, months, etc.) at the same energy level or different energy levels. Repeated treatments can be performed on the same target site or different target sites. Gaps between lesions around a circumference of a vessel can be minimized, if desired.

Implants (e.g., intrabronchial stents, compression rings, or other devices) that can compress, expand, or otherwise mechanically alter tissue to inhibit reinnervation can be used. Implants can distend airway to the airway's elastic limit, apply a desired amount of compressive forces, or the like. Pressure can be applied to destroy or otherwise injure nerve tissue. Retreatments can be performed using implants. Visualization techniques, fluorescence, and/or ultrasound can be used to assess and monitor injuries, assess size of injuries/lesions, and/or scarring to determine whether to retreat.

Immune systems can be modulated to increase or decrease scarring. Different types of drugs can be administered before, during, and/or after lesion formation to modulate the immune system.

The effective size of ablation elements can be increased by using solutions. In electrode embodiments, a hypertonic solution can increase effective electrode size. For example, a hypertonic solution can be injected, absorbed, or otherwise delivered to tissue through which energy is delivered. The temperature of tissue can be controlled to help shape lesions. Non-targeted tissue between electrodes can be frozen to help energy (e.g., RF energy) travel around the frozen tissue.

BRIEF DESCRIPTION OF THE DRAWINGS

In the Figures, identical reference numbers identify similar elements or acts.

FIG. 33 is an isometric view of a multi-component ablation assembly.

FIG. 34 is an isometric view of an expandable element ready to be inserted through a loop of an energy emitter assembly.

FIG. 35 is a side elevational view of the ablation assembly of FIG. 33.

FIG. 36 is a longitudinal cross-sectional view of the ablation assembly of FIG. 35.

DETAILED DESCRIPTION

Figure 1:
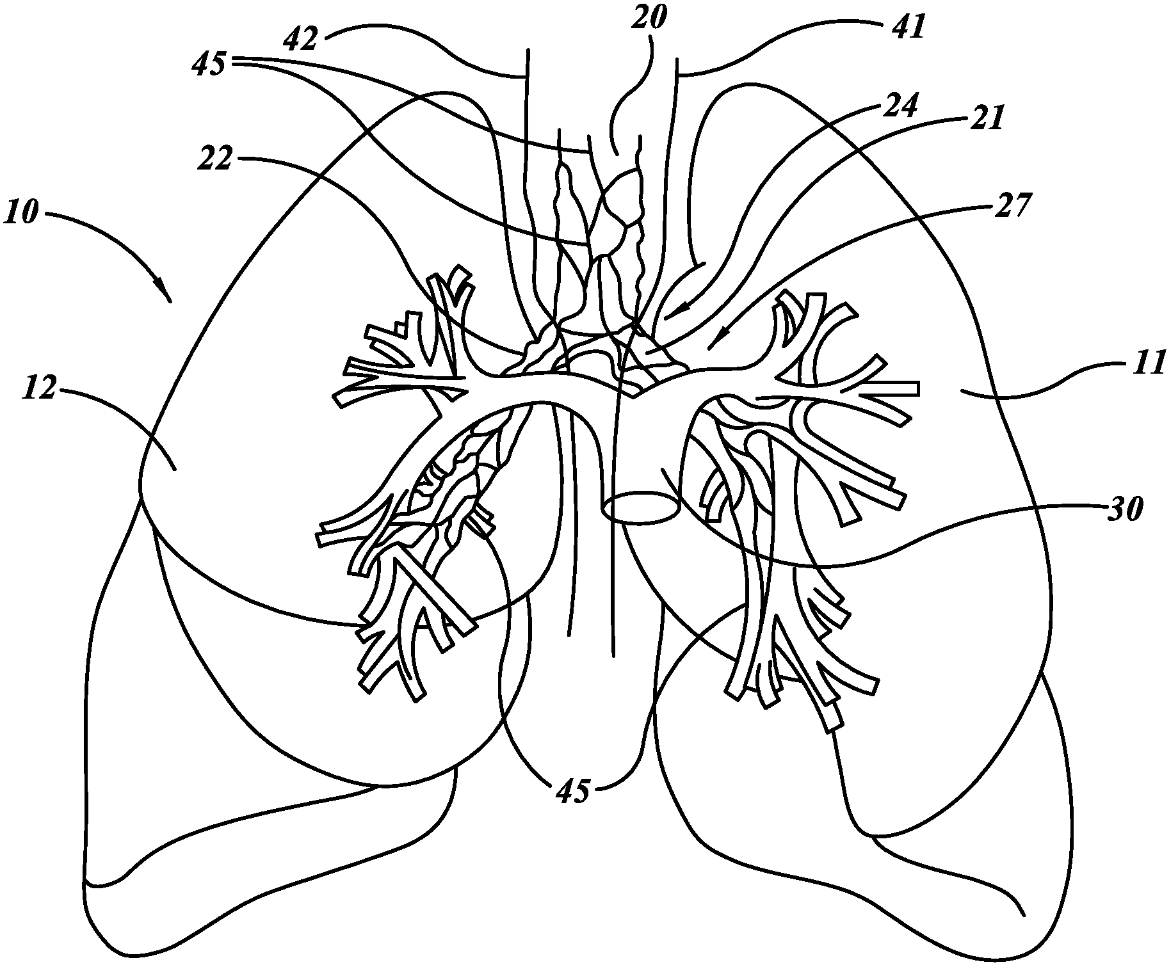
FIG. 1 is an illustration of lungs, blood vessels, and nerves near to and in the lungs.

FIG. 1 illustrates human lungs 10 having a left lung 11 and a right lung 12. A trachea 20 extends downwardly from the nose and mouth and divides into a left main bronchus 21 and a right main bronchus 22. The left main bronchus 21 and right main bronchus 22 each branch to form lobar, segmental bronchi, and sub-segmental bronchi, which have successively smaller diameters and shorter lengths in the outward direction (i.e., the distal direction). A main pulmonary artery 30 originates at a right ventricle of the heart and passes in front of a lung root 24. At the lung root 24, the artery 30 branches into a left and a right pulmonary artery, which in turn branch to form a network of branching blood vessels. These blood vessels can extend alongside airways of a bronchial tree 27. The bronchial tree 27 includes the left main bronchus 21, the right main bronchus 22, bronchioles, and alveoli. Vagus nerves 41, 42 extend alongside the trachea 20 and branch to form nerve trunks 45.

The left and right vagus nerves 41, 42 originate in the brainstem, pass through the neck, and descend through the chest on either side of the trachea 20. The vagus nerves 41, 42 spread out into nerve trunks 45 that include the anterior and posterior pulmonary plexuses that wrap around the trachea 20, the left main bronchus 21, and the right main bronchus 22. The nerve trunks 45 also extend along and outside of the branching airways of the bronchial tree 27. Nerve trunks 45 are the main stem of a nerve, comprising a bundle of nerve fibers bound together by a tough sheath of connective tissue.

The primary function of the lungs 10 is to exchange oxygen from air into the blood and to exchange carbon dioxide from the blood to the air. The process of gas exchange begins when oxygen rich air is pulled into the lungs 10. Contraction of the diaphragm and intercostal chest wall muscles cooperate to decrease the pressure within the chest to cause the oxygen rich air to flow through the airways of the lungs 10. For example, air passes through the mouth and nose, the trachea 20, then through the bronchial tree 27. The air is ultimately delivered to the alveolar air sacs for the gas exchange process.

Oxygen poor blood is pumped from the right side of the heart through the pulmonary artery 30 and is ultimately delivered to alveolar capillaries. This oxygen poor blood is rich in carbon dioxide waste. Thin semi-permeable membranes separate the oxygen poor blood in capillaries from the oxygen rich air in the alveoli. These capillaries wrap around and extend between the alveoli. Oxygen from the air diffuses through the membranes into the blood, and carbon dioxide from the blood diffuses through the membranes to the air in the alveoli. The newly oxygen-enriched blood then flows from the alveolar capillaries through the branching blood vessels of the pulmonary venous system to the heart. The heart pumps the oxygen-rich blood throughout the body. The oxygen spent air in the lung is exhaled when the diaphragm and intercostal muscles relax and the lungs and chest wall elastically return to the normal relaxed states. In this manner, air can flow through the branching bronchioles, the bronchi 21, 22, and the trachea 20 and is ultimately expelled through the mouth and nose.

Figure 2:
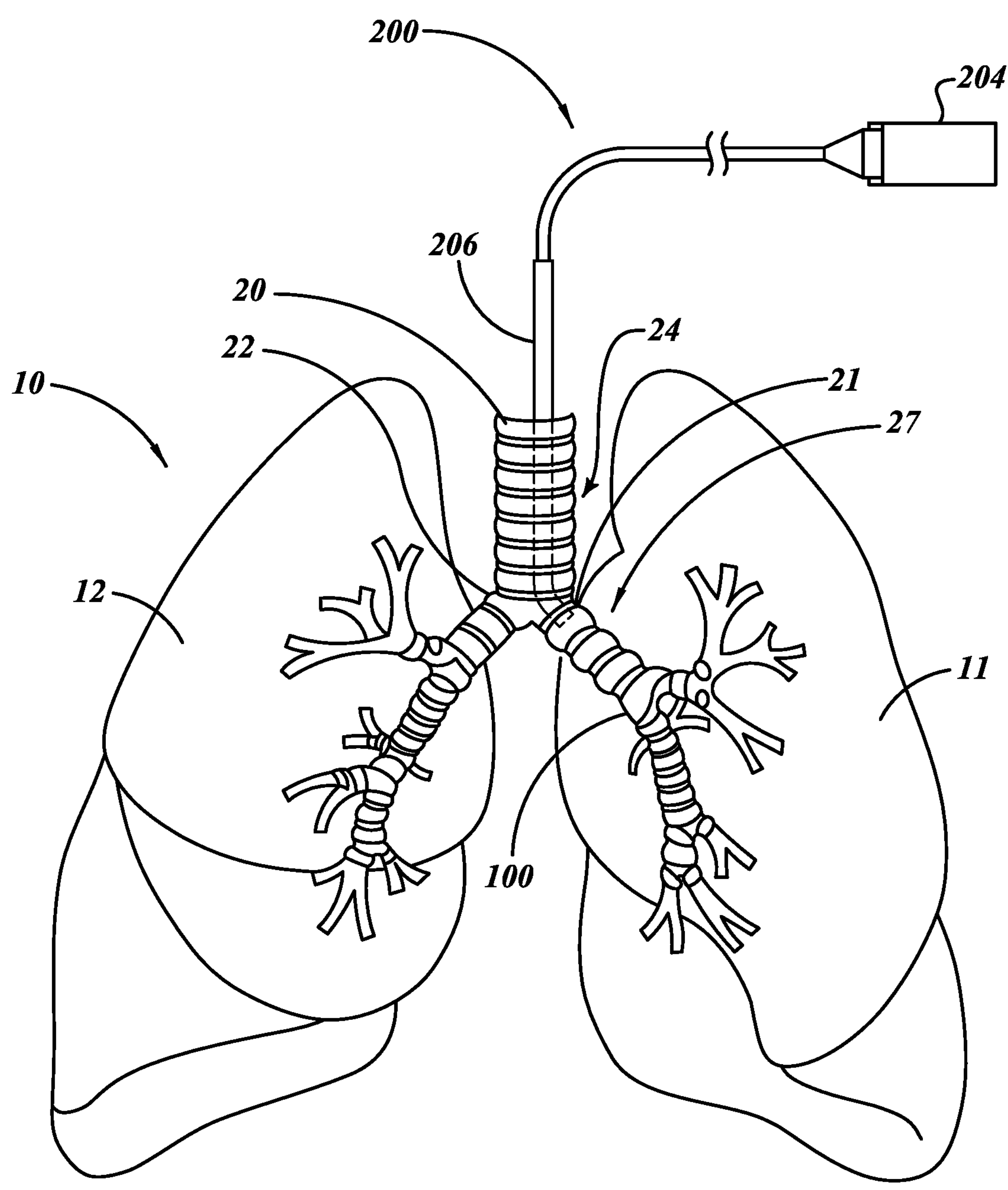
FIG. 2 is an illustration of an intraluminal treatment system positioned within a left main bronchus according to one embodiment.

FIG. 2 shows a system 200 capable of performing treatments to adjust air flow during expiration or inhalation, or both. The nervous system provides communication between the brain and the lungs 10 using electrical and chemical signals. A network of nerve tissue of the autonomic nervous system senses and regulates activity of the respiratory system and the vasculature system. Nerve tissue includes fibers that use chemical and electrical signals to transmit sensory and motor information from one body part to another. For example, the nerve tissue can transmit motor information in the form of nervous system input, such as a signal that causes contraction of muscles or other responses. The fibers can be made up of neurons. The nerve tissue can be surrounded by connective tissue, i.e., epineurium. The autonomic nervous system includes a sympathetic system and a parasympathetic system. The sympathetic nervous system is largely involved in "excitatory" functions during periods of stress. The parasympathetic nervous system is largely involved in "vegetative" functions during periods of energy conservation. The sympathetic and parasympathetic nervous systems are simultaneously active and generally have reciprocal effects on organ systems. While innervation of the blood vessels originates from both systems, innervation of the airways are largely parasympathetic in nature and travel between the lung and the brain in the right vagus nerve 42 and the left vagus nerve 41.

Any number of procedures can be performed on one or more of these nerve trunks 45 to affect the portion of the lung associated with those nerve trunks. Because some of the nerve tissue in the network of nerve trunks 45 coalesce into other nerves (e.g., nerves connected to the esophagus, nerves though the chest and into the abdomen, and the like), the treatment system 200 can treat specific sites to minimize, limit, or substantially eliminate unwanted damage of those other nerves. Some fibers of anterior and posterior pulmonary plexuses coalesce into small nerve trunks which extend along the outer surfaces of the trachea 20 and the branching bronchi and bronchioles as they travel outward into the lungs 10. Along the branching bronchi, these small nerve trunks continually ramify with each other and send fibers into the walls of the airways, as discussed in connection with FIGS. 4 and 5. Various procedures that may be performed with at least some of the devices and methods of the present invention are described in copending application Ser. No. 12/463,304 filed on May 8, 2009, which is incorporated herein by reference in its entirety.

The system 200 can affect specific nerve tissue, such as vagus nerve tissue, associated with particular sites of interest. Vagus nerve tissue includes efferent fibers and afferent fibers oriented parallel to one another within a nerve branch. The efferent nerve tissue transmits signals from the brain to airway effector cells, mostly airway smooth muscle cells and mucus producing cells. The afferent nerve tissue transmits signals from airway sensory receptors, which respond to irritants, and stretch to the brain. While efferent nerve tissue innervates smooth muscle cells all the way from the trachea 20 to the terminal bronchioles, the afferent fiber innervation is largely limited to the trachea 20 and larger bronchi. There is a constant, baseline tonic activity of the efferent vagus nerve tissues to the airways which causes a baseline level of smooth muscle contraction and mucous secretion.

In certain procedures, the system 200 can form lesions to attenuate the transmission of signals traveling along the vagus nerves 41, 42 that cause or mediate muscle contractions, mucus production, inflammation, edema, and the like. Lesions can include ablated tissue, scar tissue, openings (e.g., openings of hollow myelin sheaths), or the like. Attenuation can include, without limitation, hindering, limiting, blocking, and/or interrupting the transmission of signals. For example, the attenuation can include decreasing signal amplitude of nerve signals or weakening the transmission of nerve signals. Decreasing or stopping nervous system input to distal airways can alter airway smooth muscle tone, airway mucus production, airway inflammation, and the like, thereby controlling airflow into and out of the lungs 10. Decreasing or stopping sensory input from the airways and lungs to local effector cells or to the central nervous system can also decrease reflex bronchoconstriction, reflex mucous production, release of inflammatory mediators, and nervous system input to other cells in the lungs or organs in the body that may cause airway wall edema. In some embodiments, the nervous system input can be decreased to correspondingly decrease airway smooth muscle tone. In some embodiments, the airway mucus production can be decreased a sufficient amount to cause a substantial decrease in coughing and/or in airflow resistance. In some embodiments, the airway inflammation can be decreased a sufficient amount to cause a substantial decrease in airflow resistance and ongoing inflammatory injury to the airway wall. Signal attenuation may allow the smooth muscles to relax, prevent, limit, or substantially eliminate mucus production by mucous producing cells, and decrease inflammation. In this manner, healthy and/or diseased airways can be altered to adjust lung function. After treatment, various types of questionnaires or tests can be used to assess the subject's response to the treatment.

To treat asthma, the system 200 can target efferent parasymthetic nerves, afferent parasympathetic nerves, c-fibers, individual nerve fibers, or other nerve tissue to denervate airways of one or both lungs, denervate tissue located near the carina, or the like. Advantageously, denervating tissue near the carina can inhibit, limit, or substantially eliminate sensory input which triggers reflex central constriction and/or local constriction caused by c-fibers while sensory input for coughing and bronchoconstriction in the trachea can be maintained.

The lesions can inhibit or prevent nerve tissue regrowth for extended efficacy. In some procedures, lesions alter respiratory function for at least about 6 months, 8 months, 10 months, 1 year, 2 years, or other desired period of time. If nerve tissue regenerates and leads to functional recovery that results in unwanted construction of airways, additional procedures can be performed to injure the regenerated nerve tissue. Repeated injury can further inhibit or prevent nerve tissue regrowth.

Main bronchi 21, 22 (i.e., airway generation 1) of FIGS. 1 and 2 can be treated to affect distal portions of the bronchial tree 27. In some embodiments, the left and right main bronchi 21, 22 are treated at locations along the left and right lung roots 24 and outside of the left and right lungs 11, 12. Treatment sites can be distal to where vagus nerve branches connect to the trachea and the main bronchi 21, 22 and proximal to the lungs 11, 12. A single treatment session involving two therapy applications can be used to treat most of or the entire bronchial tree 27. Substantially all of the bronchial branches extending into the lungs 11, 12 may be affected to provide a high level of therapeutic effectiveness. Because the bronchial arteries in the main bronchi 21, 22 have relatively large diameters and high heat sinking capacities, the bronchial arteries may be protected from unintended damage due to the treatment.

Figure 3:
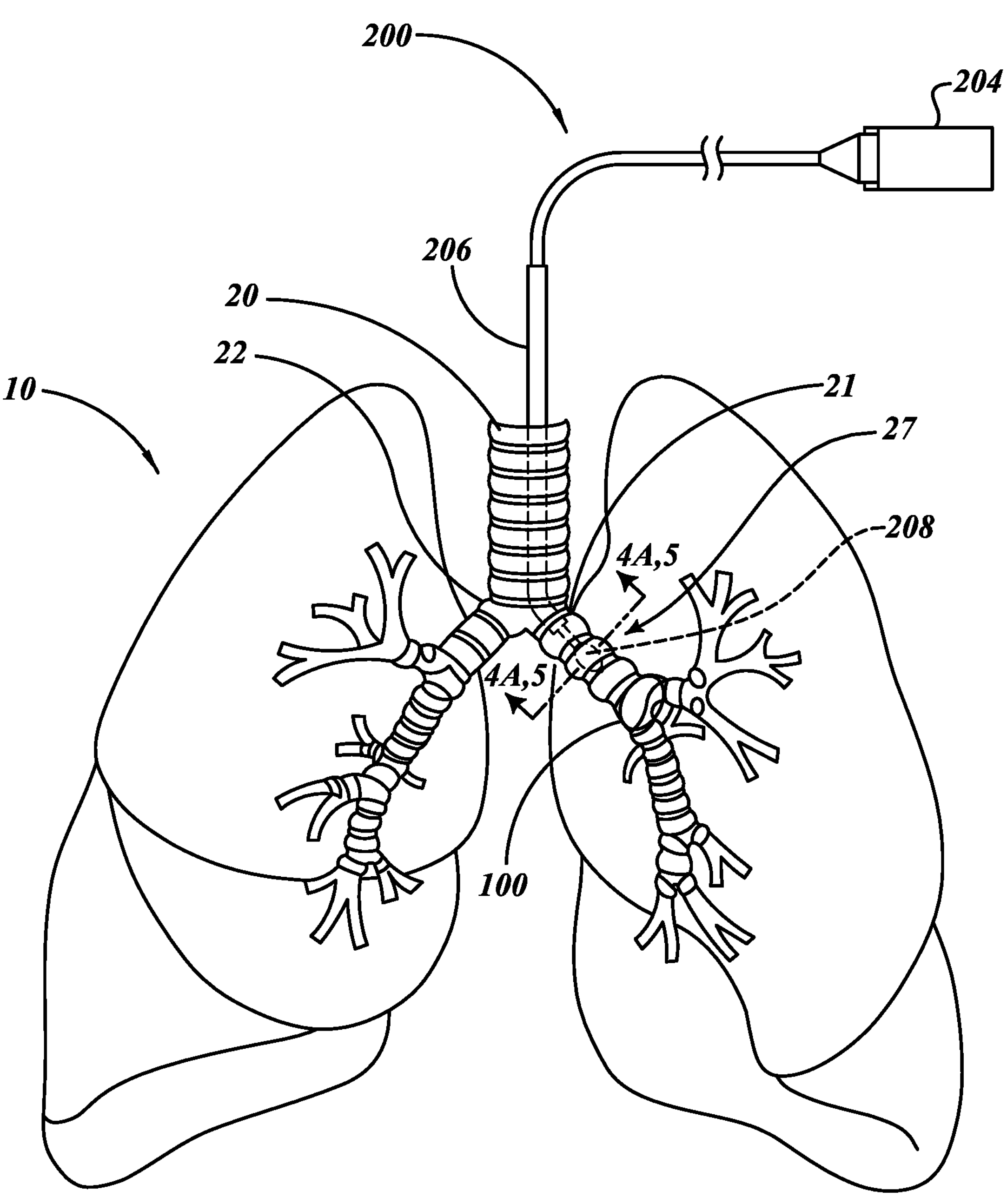
FIG. 3 is an illustration of a delivery device extending from a delivery apparatus positioned in the left main bronchus.
Figure 4A:
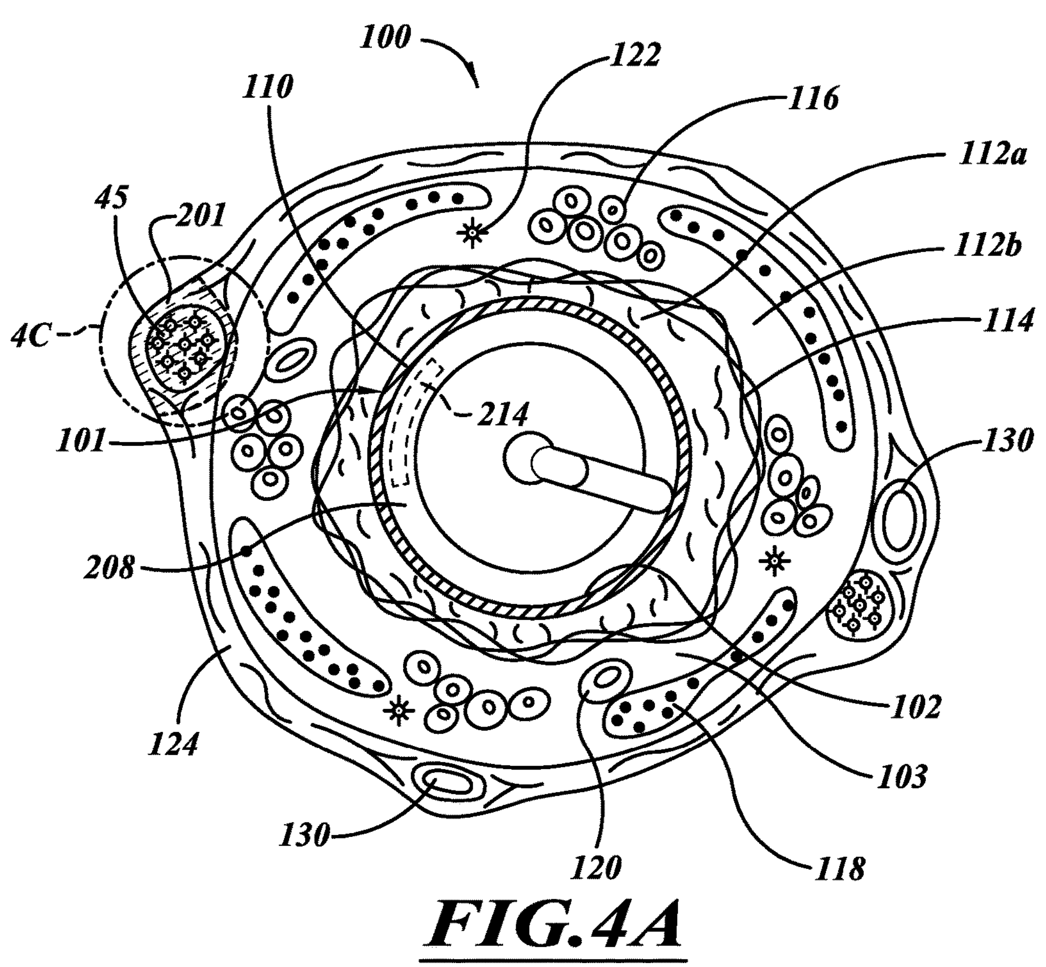
FIG. 4A is a cross-sectional view of an airway and an ablation assembly positioned along an airway lumen.

FIGS. 3 and 4A show a catheter 204 extending through an apparatus 206. The catheter 204 can injure nerve tissue proximate to or within the main bronchi 21, 22, as well as airways that are distal to the main bronchi 21, 22. An ablation assembly 208 can be positioned outside the lung within the right or left main bronchi, the lobar bronchi, and bronchus intermedius. The intermediate bronchus is the portion of the right main bronchus and between the upper lobar bronchus and the origin of the middle and lower lobar bronchi. The ablation assembly 208 can be positioned in higher generation airways (e.g., airway generations >2) to affect remote distal portions of the bronchial tree 27. The catheter system 204 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

Each segmental bronchus may be treated by delivering energy to a single treatment site along the segmental bronchus. For example, the catheter system 204 can deliver energy to each segmental bronchus of the right lung. In some procedures, ten applications of energy can treat most of or substantially all of the right lung. In some procedures, most or substantially all of both lungs are treated using less than thirty-six different applications of energy. Depending on the anatomical structure of the bronchial tree, segmental bronchi can often be denervated using one or two applications of energy.

Function of other tissue or anatomical features, such as the mucous glands, cilia, smooth muscle, body vessels (e.g., blood vessels), and the like can be maintained when nerve tissue is injured. Nerve tissue includes nerve cells, nerve fibers, dendrites, and supporting tissue, such as neuroglia. Nerve cells transmit electrical impulses, and nerve fibers are prolonged axons that conduct the impulses. The electrical impulses are converted to chemical signals to communicate with effector cells or other nerve cells. By way of example, a portion of an airway of the bronchial tree 27 can be denervated to attenuate one or more nervous system signals transmitted by nerve tissue. Denervating can include damaging all of the nerve tissue of a section of a nerve trunk along an airway to stop substantially all the signals from traveling through the damaged section of the nerve trunk to more distal locations along the bronchial tree or signals from distal regions of the bronchial tree to the central nervous system. Additionally, signals that travel along nerve fibers that go directly from sensory receptors (e.g., cough and irritant receptors) in the airway to nearby effector cells (e.g., postganglionic nerve cells, smooth muscle cells, mucous cells, inflammatory cells, and vascular cells) will also be stopped. If a plurality of nerve trunks extends along the airway, each nerve trunk can be damaged. As such, the nerve supply along a section of the bronchial tree can be cut off. When the signals are cut off, the distal airway smooth muscle can relax, leading to airway dilation, causing mucous cells to decrease mucous production, or causing inflammatory cells to stop producing airway wall swelling and edema. These changes reduce airflow resistance so as to increase gas exchange in the lungs 10, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

In some embodiments, one of the left and right main bronchi 21, 22 is treated to treat one side of the bronchial tree 27. The other main bronchus 21, 22 can be treated based on the effectiveness of the first treatment. For example, the left main bronchus 21 can be treated to treat the left lung 11. The right main bronchus 22 can be treated to treat the right lung 12. In some embodiments, a single treatment system can damage the nerve tissue of one of the bronchi 21, 22 and can damage the nerve tissue of the other main bronchus 21, 22 without removing the treatment system from the trachea 20. Nerve tissue positioned along the main bronchi 21, 22 can thus be damaged without removing the treatment system from the trachea 20. In some embodiments, a single procedure can be performed to conveniently treat substantially all, or at least a significant portion (e.g., at least 50%, 70%, 80%, 90% of the bronchial airways), of the patient's bronchial tree. In other procedures, the treatment system can be removed from the patient after treating one of the lungs 11, 12. If needed, the other lung 11, 12 can be treated in a subsequent procedure.

FIG. 4A is a transverse cross-sectional view of a healthy airway 100 with a lesion comprising scar tissue 201, illustrated in dashed line. As shown in the enlarged cross-section of the lesion in FIG. 4C, the nerve trunk 45 includes fascicles 115 protected by an epineurium 116. The fascicles 115 include nerve fibers 109 and a perineurium 107 surrounding the fibers 109. The nerve fibers 109 have axons, myelin that surrounds and insulates each of the axons, and endoneurium 113.

The nerve trunk 45 has the ability to regenerate. Neuroregeneration may include, for example, remyelination and formation of new neurons, glia, axons, myelin, and/or synapses. If axons are damaged, the axons can retract and neurons can undergo a relatively short dormant phase. The neurons can then be activated for axon regeneration. Severe injuries, such as a Type 3 injury or greater as discussed below, can inhibit reinnervation.

Type 1 nerve injuries involve neurapraxia that typically involves demyelination with an intact nerve. There is no interruption of axonal or connective tissue continuity. Remyelination can occur resulting in about 100% recovery.

Type 2 nerve injuries involve axonotmesis that is often characterized by axonal disruption with intact connective tissue sheaths. Endoneurial microstructure is maintained, often resulting in complete functional regeneration of axons. There is about 90% recovery.

Type 3 nerve injuries are characterized by discontinuity of endoneurial microstructures including injuries to axons, and may involve endoneurial scarring. There is generally no injury to the perineurium. Recovery from such an injury may be dependent upon the extent of the injury. A relatively long lesion formed by a Type 3 injury may prevent functional regeneration of nerve tissue. Scar tissue can form to help prevent reinnervation. There is often less than 60% recovery.

A Type 4 nerve injury is a complete injury to nerve fibers and often involves significant scarring contained within the epineurium 113. Regeneration of axons is difficult because substantially the entire population of axons within a fascicle are blocked by scar tissue. A fourth degree injury involves injury to the axon, myelin, endoneurium, and perineurium. There is often less than about 10% to about 20% recovery.

A Type 5 injury occurs when nerve fiber and axons in all connective tissue elements are divided or severed. A complete transection is a Type 5 injury. Nerves typically do not regenerate after complete transection. Thus, there is typically no functional recovery.

The methods and systems of at least some embodiments of the invention enable the selection of the desired type of injury based on various factors including the power level, lesion size, lesion location, number of lesions, and lesion composition to achieve a desired effective length of treatment. By way of example, lesion 201 can be a Type 3 or greater nerve injury that involves disruption of axon sheaths and the formation of scar tissue in the endoneurium. This alters respiratory function of a region of the lung distal to the injury site for a significant length of time (for example, at least about 6 months). In some procedures, substantially all of the axons of the fascicle 115, myelin, and endoneurium 113 are destroyed. Scar tissue replaces the destroyed tissue. In some procedures, all of the axons of the fascicle 115, the myelin, and endoneurium 113 are ablated and replaced by scar tissue. Denervation can include targeting efferent parasymthetic nerves, afferent parasympathetic nerves, c-fibers, or other nerve tissue to denervate airways of one or both lungs. The system can inhibit afferent c-fiber reinnervation, without or without efferent reinnervation.

Referring again to FIG. 4A, the airway 100 includes inner surface 102 is defined by a folded layer of epithelium 110 surrounded by stroma 112*a*. A layer of smooth muscle tissue 114 surrounds the stroma 112*a*. A layer of stroma 112*b* is between the muscle tissue 114 and connective tissue 124. Mucous glands 116, cartilage plates 118, blood vessels 120, and nerve fibers 122 are within the stroma layer 112*b*. Bronchial artery branches 130 and nerve trunks 45 are exterior to a wall 103 of the airway 100. The illustrated arteries 130 and nerve trunks 45 are within the connective tissue 124 surrounding the airway wall 103 and can be oriented generally parallel to the airway 100. In FIG. 1, for example, the nerve trunks 45 originate from the vagus nerves 41, 42 and extend along the airway 100 towards the air sacs. The nerve fibers 122 are in the airway wall 103 and extend from the nerve trunks 45 to the muscle tissue 114. Nervous system signals are transmitted from the nerve trunks 45 to the muscle 114 and mucous glands 116 via the nerve fibers 122. Additionally, signals are transmitted from sensory receptors (e.g., cough, irritant, and stretch) through the nerve trunks 45 to the central nervous system.

Cilia can be damaged, excited, or otherwise altered to elicit a desired response along the epithelium 110 in order to control (e.g., increase or decrease) mucociliary transport. Many particles are inhaled as a person breathes, and the airways function as a filter to remove the particles from the air. The mucociliary transport system functions as a self-cleaning mechanism for all the airways throughout the lungs 10. The mucociliary transport is a primary method for mucus clearance from distal portions of the lungs 10, thereby serving as a primary immune barrier for the lungs 10. For example, the inner surface 102 of FIG. 4A can be covered with cilia and coated with mucus. As part of the mucociliary transport system, the mucus entraps many inhaled particles (e.g., unwanted contaminates such as tobacco smoke) and moves these particles towards the larynx. The ciliary beat of cilia moves a continuous carpet of mucus and entrapped particles from the distal portions of the lungs 10 past the larynx and to the pharynx for expulsion from the respiratory system.

If an ablation element is an RF electrode 214, the electrode 214 can be brought into contact with or proximate to the inner surface 102. The RF electrode 214 can output RF energy which travels through the tissue and is converted into heat. The heat causes scarring. The RF energy can be directed radially outward towards the nerve trunk 45 and between the adjacent cartilage plates 118 to mitigate or avoid appreciable damage to the cartilage plates 118. Damage to other non-targeted regions (e.g., the epithelium) can also be kept at or below an acceptable level.

Natural body functions can help prevent, reduce, or limit damage to tissue. Blood within the blood vessels 130 can absorb thermal energy and can then carry the thermal energy away from the heated section of the branches 130. In this manner, blood can mitigate or avoid damage to the blood vessels 130. After the treatment is performed, the bronchial artery branches 130 can continue to maintain the health of lung tissue. In some embodiments, a sufficient amount of RF energy is delivered to the nerve trunk 45 to destroy an entire longitudinal section of the nerve trunk 45 while keeping the amount of energy that reaches the blood vessels 130 below an amount that causes tissue destruction of the vessel 130. Thus, therapies can be performed without damaging to any significant extent other regions of the airway 100, even regions that are adjacent to the treatment site.

Figure 4B:
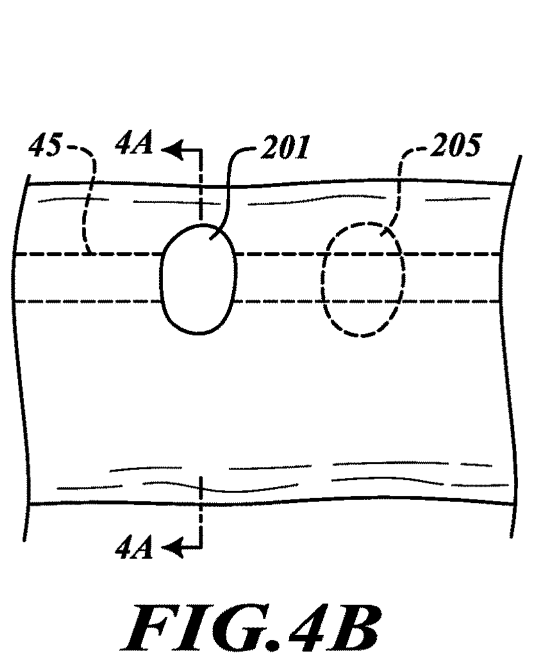
FIG. 4B is a side elevational view of the airway of FIG. 4A.
Figure 4C:
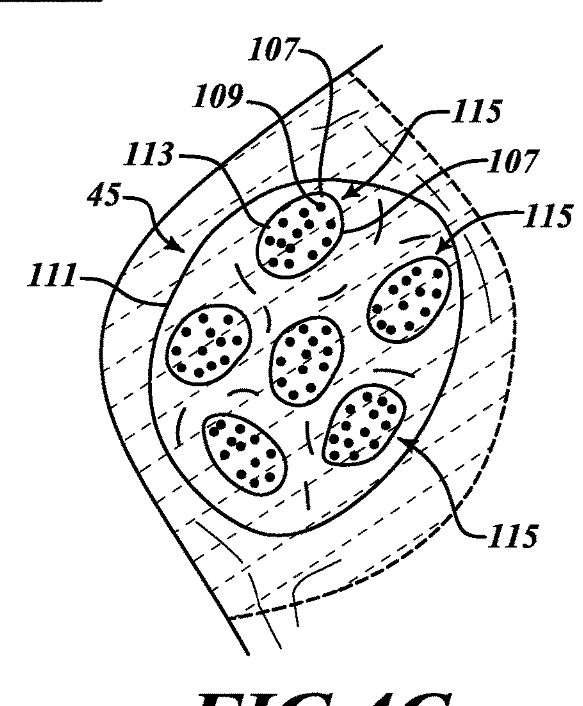
FIG. 4C is a cross-sectional view of a nerve trunk.

Treatment efficacy can be evaluated based at least in part on one or more airway attributes, pulmonary function tests, exercise capacity tests, and/or questionnaires. Patients can be evaluated to track and monitor their progress. If needed or desired, additional procedures can be performed until desired responses are achieved. Different types of instruments for evaluating airway attributes may be used. If a desired amount of airway dilation is not achieved, additional lesions can be formed. Lesions can connect to form a large lesion, making it unlikely for enough tissue regrowth for functional recovery. Alternatively, lesions make it difficult for axons to reach open myelin sheaths, if any, that would facilitate regrowth. The number, dimensions, and positions of the lesions can be selected to inhibit or prevent axons from being able to regrow along the entire length of a nerve trunk. FIG. 4B shows a second lesion 205, illustrated in dashed line, spaced apart from the lesion 201. The spacing and size of each lesion 201, 205 may be selected to minimize the chance of nerve regeneration.

Different attributes of airways can be evaluated to determine procedures to be performed. Such airway attributes include, without limitation, physical properties of airways (e.g., airway compliance, contractile properties, etc.), airway resistance, dimensions of airway lumens (e.g., shapes of airways, diameters of airways, etc.), responsiveness of airways (e.g., responsiveness to stimulation), muscle characteristics (e.g., muscle tone, muscle tension, etc.), inflammatory cells, inflammatory cytokines, or the like. In some embodiments, changes of airway muscle characteristics can be monitored by measuring pressure changes in the ablation assembly 208, which is inflated to a known pressure. Based on pressure changes, a physician determines the effects, if any, of the treatment, including, without limitation, whether targeted tissue has been stimulated, ablated, or the like.

Figure 5:
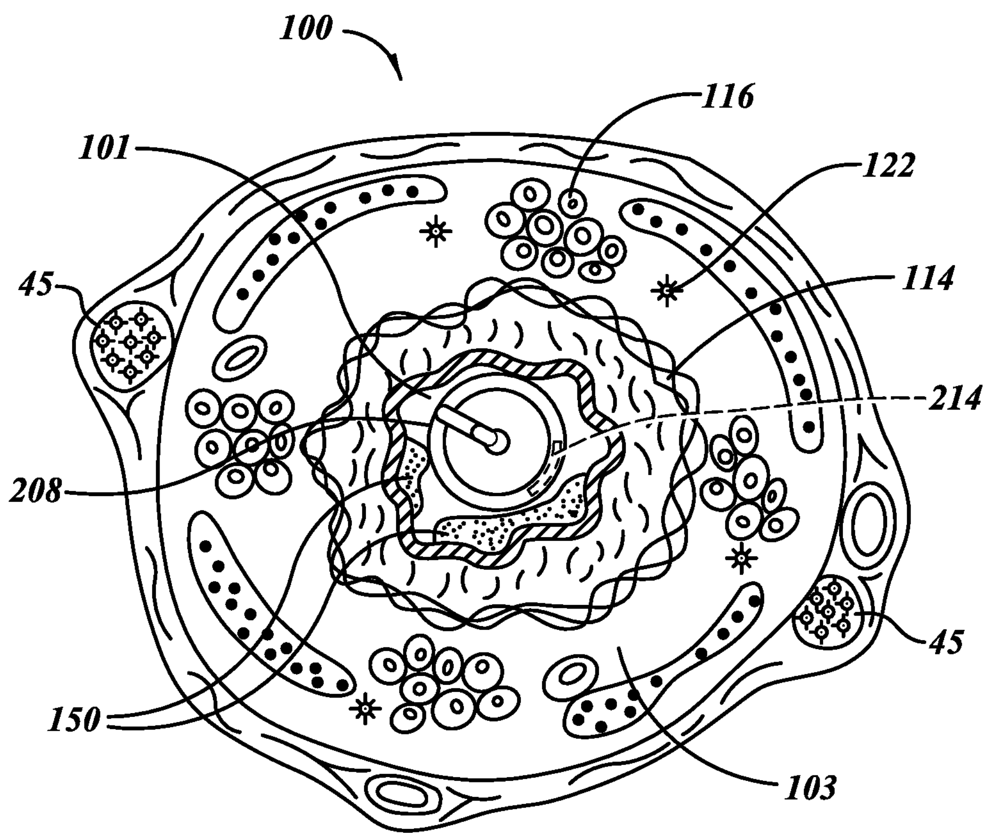
FIG. 5 is a cross-sectional view of an airway when smooth muscle of the airway is constricted and mucus is in an airway lumen.

FIG. 5 is a transverse cross-sectional view of a portion of the airway 100 that has smooth muscle tissue 114 in a contracted state, mucus 150 from hypertrophied mucous glands 116, and inflammatory swelling and edema fluid thickening the airway wall 103. The contracted muscle tissue 114, the mucus 150, and thickened airway wall 103 cooperate to partially obstruct the lumen 101 resulting in a relatively high air flow resistance. The nerve trunk 45 is damaged to relax the muscle tissue 114 to dilate the airway 100 to reduce air flow resistance, thereby allowing more air to reach the alveolar sacs for the gas exchange process. Decreases in airway resistance may indicate that passageways of airways are opening, for example in response to attenuation of nervous system input to those airways. The decrease of airway resistance associated with treating low generation airways (e.g., main bronchi, lobar bronchi, segmental bronchi) may be greater than the amount of decrease of airway resistance associated with treating high generation airways (e.g., subsegmental bronchioles). A physician can select appropriate airways for treatment to achieve a desired decrease in airway resistance, which can be measured at a patient's mouth, a bronchial branch that is proximate to the treatment site, a trachea, or any other suitable location. The airway resistance can be measured before performing the therapy, during the therapy, and/or after the therapy. In some embodiments, airway resistance is measured at a location within the bronchial tree by, for example, using a vented treatment system that allows for respiration from areas that are more distal to the treatment site.

Energy can be used to damage target regions, promote scar tissue, inhibit reinnervation, or the like. As used herein, the term "energy" is broadly construed to include, without limitation, thermal energy, cryogenic energy (e.g., cooling energy), electrical energy, acoustic energy (e.g., ultrasonic energy), radio frequency energy, pulsed high voltage energy, mechanical energy, ionizing radiation, optical energy (e.g., light energy), and combinations thereof, as well as other types of energy suitable for treating tissue. In some embodiments, the catheter system 204 delivers energy and one or more substances (e.g., radioactive seeds, radioactive materials, etc.), treatment agents, and the like. Exemplary non-limiting treatment agents include, without limitation, one or more antibiotics, anti-inflammatory agents, pharmaceutically active substances, bronchoconstrictors, bronchodilators (e.g., beta-adrenergic agonists, anticholinergics, etc.), nerve blocking drugs, photoreactive agents, or combinations thereof. For example, long acting or short acting nerve blocking drugs (e.g., anticholinergics) can be delivered to the nerve tissue to temporarily or permanently attenuate signal transmission. Substances can also be delivered directly to the nerves 122 or the nerve trunks 45, or both, to chemically damage the nerve tissue.

Figure 6:
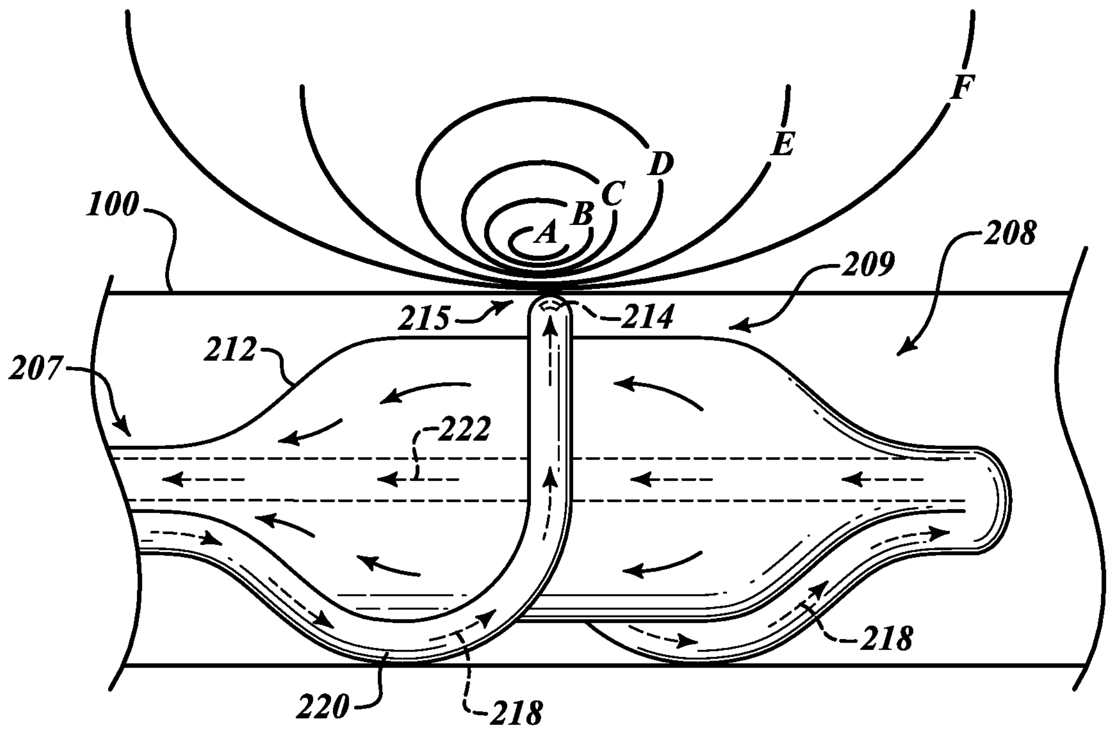
FIG. 6 is a graph of the depth of tissue versus the temperature of the tissue.
Figure 7:
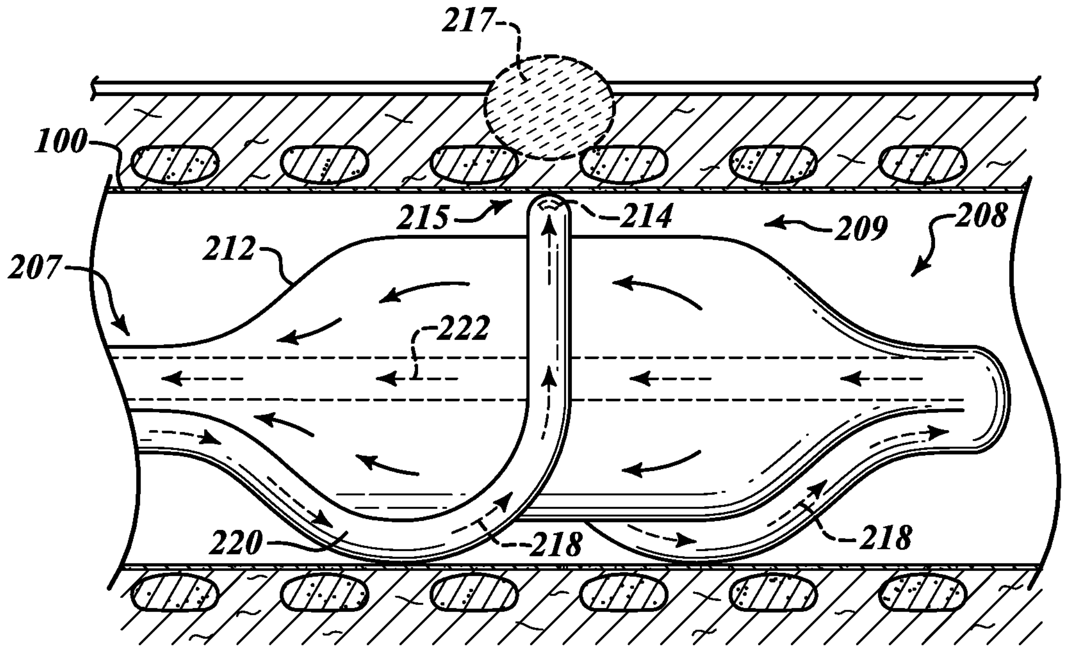
FIG. 7 is a side elevational view of an ablation assembly in an airway.

FIGS. 6 and 7 show the effect produced by superficial and deep heating by RF energy and superficial cooling by circulating coolant in an ablation assembly 208 of the system 200. A cooling section 209 of the ablation assembly 208 contains coolant to cool tissue adjacent to a tissue-contacting portion 215 of the energy emitter assembly 220 when energy is outputted. The cooling section 209 can absorb a sufficient amount of thermal energy from the airway wall 100 to limit or prevent damage to the tissue between the energy emitter assembly 220 and the nerve tissue or other targeted tissue.

The terms "ablate" or "ablation," including derivatives thereof, include, without limitation, substantial altering of electrical properties, mechanical properties, chemical properties, or other properties of tissue. As used herein, the term "ablate," including variations thereof, refers, without limitation, to destroying or to permanently damaging, injuring, or traumatizing tissue. For example, ablation may include localized tissue destruction, cell lysis, cell size reduction, necrosis, or combinations thereof. In the context of pulmonary ablation applications, the term "ablation" includes sufficiently altering nerve tissue properties to substantially block transmission of electrical signals through the ablated nerve tissue. Ablated tissue is often replaced with scar tissue.

In FIG. 7, arrows 218 represent movement of the coolant through the energy emitter assembly 220. Arrows 222 represent movement of the coolant through a deployable element, illustrated as a distensible and thermally conductive balloon 212. Isothermal curves show the temperatures that are reached at the electrode 214 and at different depths into the airway wall 100 from the electrode-tissue interface when power is applied to the electrode 214 and coolant (e.g., a room temperature saline solution or iced saline) is delivered to the balloon 212. The term "element" in the context of "expandable element" includes a discrete element or a plurality of discrete elements. By way of example, an expandable element can be a single balloon or a plurality of balloons in fluid communication with one another.

By adjusting the rate of power delivery to the electrode 214, the rate at which coolant (e.g., saline solution) is passed into the balloon 212, the temperature of the saline solution, and the size of the balloon 212, the exact contour and temperature of the individual isotherms can be modified. For example, by selecting the proper temperature and flow rate of saline and the rate of power delivery to the electrode, it is possible to achieve temperatures in which isotherm A=60° C., B=55° C., C=50° C., D=45° C., E=40° C., and F=37° C. To form the scar 217 in FIG. 7, the electrode 214 can receive and output about 10 watts to about 30 watts for about 30 seconds to about 240 seconds. In some procedures, about 15 watts to about 25 watts can be delivered to the electrode 214 for about 60 seconds to about 80 seconds. The total energy dosage, in some procedures, can be about 300 Joules to about 7,200 Joules. The position of the electrode(s) and the total energy dosage can be adjusted to obtain lesions of different densities, shapes, and locations. It should be noted that many structures (e.g., nerve branches, cartilage plates, vessels, etc.) are not shown in FIG. 7.

Further adjustments make it possible to achieve temperatures where isotherm A=50° C., B=47.5° C., C=45° C., D=42.5° C., E=40° C., and F=37° C. Only those areas contained within the 50° C. isotherm will be heated enough to induce cell death. In some procedures, tissue at a depth of about 2 mm to about 8 mm in the airway wall can be ablated while other non-targeted tissues at a depth less than 2 mm in the airway wall are kept at a temperature below at temperature that would cause cell death. The coolant 218 can absorb energy to cool the tissue-contacting portion 215 of the energy emitter assembly 220 while the balloon 212 holds the energy emitter assembly 220 against the airway 100.

Figure 8:
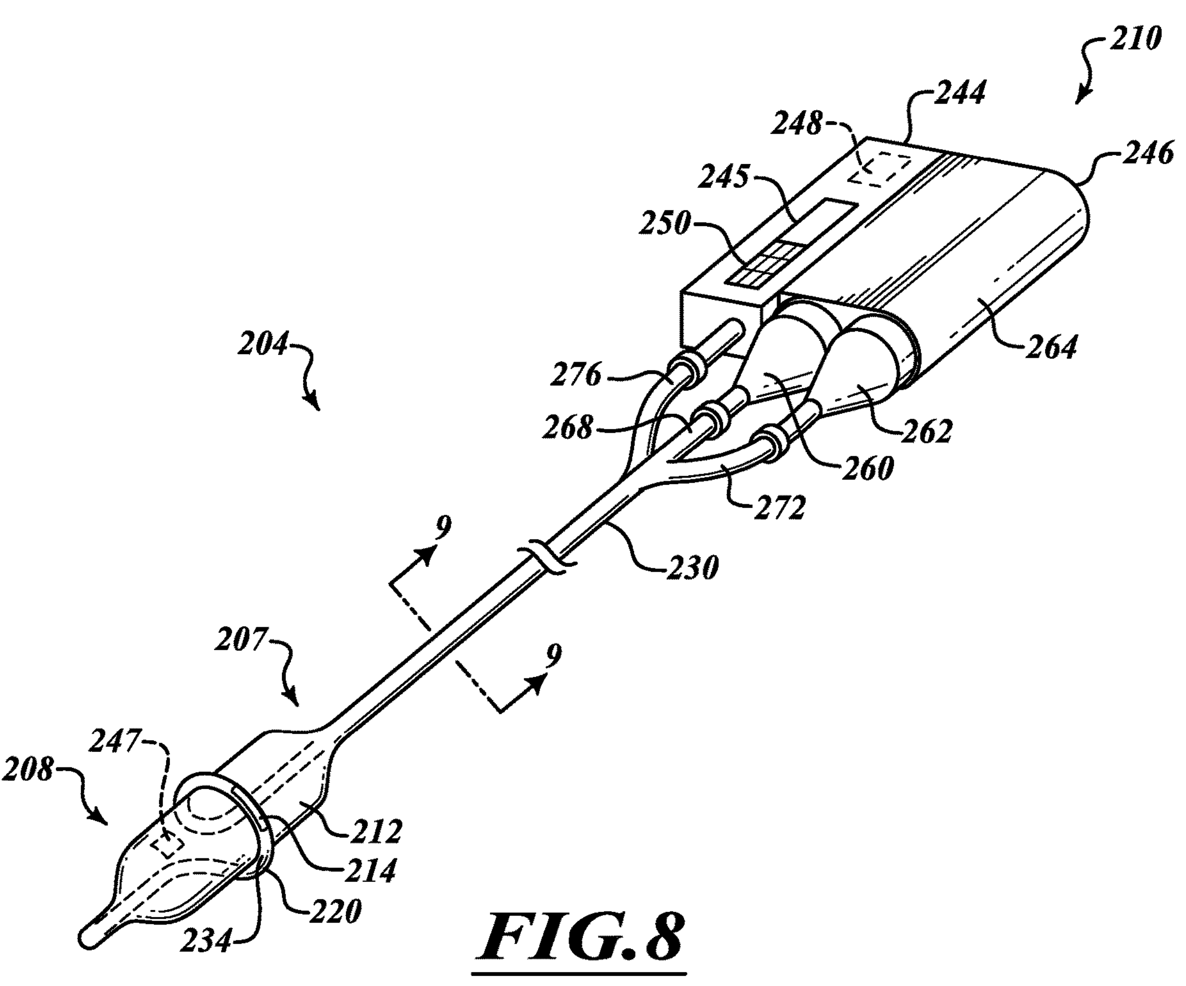
FIG. 8 is an isometric view of a delivery device according to one embodiment.

Referring to FIG. 8, the catheter system 204 includes a control module 210 coupled to a catheter 207 having an elongate body in the form of a shaft 230 and the ablation assembly 208 coupled to the distal end of the shaft 230. Ablation assembly 208 comprises an energy emitter assembly 220 extending from the elongate shaft 230 and wrapping around the balloon 212. The balloon 212 can be inflated from a collapsed state to the illustrated expanded state. As the balloon 212 inflates, the electrode 214 can be moved towards the airway wall. The inflated balloon 212 can help hold the electrode 214 near (e.g., proximate or in contact with) tissue through which energy is delivered. The coolant can absorb thermal energy to cool the balloon 212 or the energy emitter assembly 220, or both. This in turn cools the outer surface of the airway wall.

The control module 210 generally includes a controller 244 and a fluid delivery system 246. The controller 244 includes, without limitation, one or more processors, microprocessors, digital signal processors (DSPs), field programmable gate arrays (FPGA), and/or application-specific integrated circuits (ASICs), memory devices, buses, power sources, and the like. For example, the controller 244 can include a processor in communication with one or more memory devices. Buses can link an internal or external power supply to the processor. The memories may take a variety of forms, including, for example, one or more buffers, registers, random access memories (RAMs), and/or read only memories (ROMs). The controller 244 may also include a display 245, such as a screen, and an input device 250. The input device 250 can include a keyboard, touchpad, or the like and can be operated by a user to control the catheter 207.

The controller 244 can store different programs. A user can select a program that accounts for the characteristics of the tissue and desired target region. For example, an air-filled lung can have relatively high impedance, lymph nodes can have medium impedance, and blood vessels can have relatively low impedance. The controller 244 can determine an appropriate program based on the impedance. A differential cooling program can be executed to deliver different temperature coolants through the balloon 212 and the energy emitter assembly 220. The temperature difference can be at least 10° C. Performance can be optimized based on feedback from sensors that detect temperatures, tissue impedance, or the like. For example, the controller 244 can control operation of the ablation assembly 208 based on a surface temperature of the tissue to which energy is delivered. If the surface temperature becomes excessively hot, cooling can be increased and/or electrode power decreased in order to produce deep lesions while protecting surface tissues. The controller 244 can also be programmed to control the amount of energy delivered from a power source 248 to the energy emitter to injure targeted tissue and promote the formation of scar tissue. Different programs can be used to generate overlapping lesions, spaced-apart lesions, adjust lesion density, or the like.

The internal power supply 248 (illustrated in dashed line in FIG. 8) can supply energy to the electrode 214 and can be an energy generator, such as a radiofrequency (RF) electrical generator. RF energy can be outputted at a desired frequency. Example frequencies include, without limitation, frequencies in a range of about 50 KHZ to about 1,000 MHZ. When the RF energy is directed into tissue, the energy is converted within the tissue into heat causing the temperature of the tissue to be in the range of about 40° C. to about 99° C. The RF energy can be applied for about 1 second to about 120 seconds. In some embodiments, the RF generator 248 has a single channel and delivers approximately 1 to 25 watts of RF energy and possesses continuous flow capability. Other ranges of frequencies, time intervals, and power outputs can also be used. Alternatively, the internal power supply 248 can be an energy storage device, such as one or more batteries. Electrical energy can be delivered to the energy emitter assembly 220, which converts the electrical energy to RF energy or another suitable form of energy. Other forms of energy that may be delivered include microwave, ultrasound, direct current, or laser energy. Alternatively, cryogenic ablation may be utilized wherein a fluid at cryogenic temperatures is delivered through the shaft 230 to cool a cryogenic heat exchanger on the ablation assembly 208.

The fluid delivery system 246 includes a fluid source 260 coupled to a supply line 268 and a fluid receptacle 262 coupled to a return line 272. The fluid source 260 can include a container (e.g., a bottle, a canister, a tank, or other type of vessel for holding fluid) held in a housing unit 264. In pressurizable embodiments, the fluid source 260 includes one or more pressurization devices (e.g., one or more pumps, compressors, or the like) that pressurize coolant. Temperature control devices (e.g., Peltier devices, heat exchangers, or the like) can cool or recondition the fluid. The fluid can be a coolant comprising saline, de-ionized water, refrigerant, cryogenic fluid, gas, or the like. In other embodiments, the fluid source 260 can be an insulated container that holds and delivers a chilled coolant to the supply line 268. The coolant flows distally through the elongate shaft 230 into the ablation assembly 208. Coolant in the ablation assembly 208 flows proximally through the elongate shaft 230 to the return line 272. The coolant proceeds along the return line 272 and ultimately flows into the fluid receptacle 262.

The balloon 212 optionally has a sensor 247 (illustrated in dashed line) that is communicatively coupled to the controller 244. The controller 244 can command the catheter 207 based on signals from the sensor 247 (e.g., a pressure sensor, a temperature sensor, a thermocouple, a pressure sensor, a contact sensor, or the like). Sensors can also be positioned on energy emitter assembly 220, along the elongate shaft 230 or at any other location. The controller 244 can be a closed loop system or an open loop system. For example, in a closed loop system, the electrical energy is delivered to the electrode 214 based upon feedback signals from one or more sensors configured to transmit (or send) one or more signals indicative of one or more tissue characteristics, energy distribution, tissue temperatures, or any other measurable parameters of interest. Based on those readings, the controller 244 adjusts operation of the electrode 214. Alternatively, in an open loop system, the operation of the electrode 214 is set by user input. For example, the user can observe tissue temperature or impedance readings and manually adjust the power level delivered to the electrode 214. Alternatively, the power can be set to a fixed power mode. In yet other embodiments, a user can repeatedly switch between a closed loop system and an open loop system.

To effectively cool the electrode 214, a conduit 234 coupled to the electrode 214 is fluidly coupled to a coolant delivery lumen within the shaft 230 to receive coolant therefrom. Alternatively, flow diverters within the balloon 212 can direct some or all of the coolant in the balloon 212 towards the electrode 214 or a balloon sidewall and may provide a separate cooling channel for the electrode 214. In some embodiments, one or more cooling channels extend through the electrode 214 (e.g., electrode 214 may be tubular so that coolant can flow through it). In other embodiments, the coolant flows around or adjacent the electrode 214. For example, an outer member, illustrated as a conduit 234 in FIG. 8, can surround the electrode 214 such that fluid can flow between the electrode 214 and the conduit 234. Additionally or alternatively, the ablation assembly 208 can be actively cooled or heated using one or more thermal devices (e.g., Peltier devices), cooling/heating channels, or the like.

Figure 9:
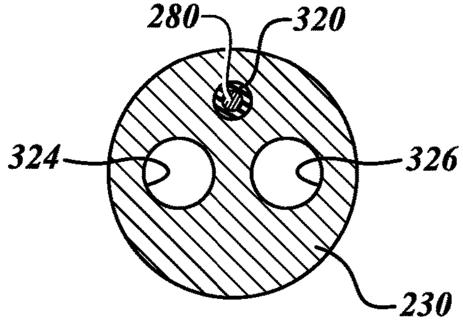
FIG. 9 is a cross-sectional view of an elongate body taken along a line 9-9 of FIG. 8.

Referring to FIGS. 8 and 9, the elongate shaft 230 extends from the control module 210 to the ablation assembly 208 and includes a power line lumen 320, a delivery lumen 324, and a return lumen 326. A power line 280 extends through the power line lumen 320 and couples the controller 244 to the electrode 214. The delivery lumen 324 provides fluid communication between the fluid source 260 and the energy emitter assembly 220 and balloon 212. The return lumen 326 provides fluid communication between the balloon 212 and/or electrode 214 and the fluid receptacle 262. The elongate shaft 230 can be made, in whole or in part, of one or more metals, alloys (e.g., steel alloys such as stainless steel), plastics, polymers, and combinations thereof, as well as other biocompatible materials, and can be flexible to pass conveniently along highly branched airways. Sensors can be embedded in the elongate shaft 230 to detect the temperature of the fluids flowing therethrough.

Figure 10:
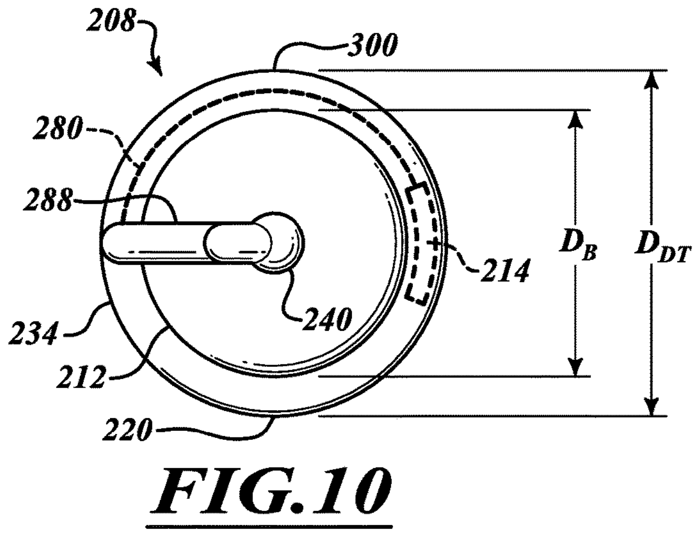
FIG. 10 is a front elevational view of the delivery device of FIG. 9.
Figure 11:
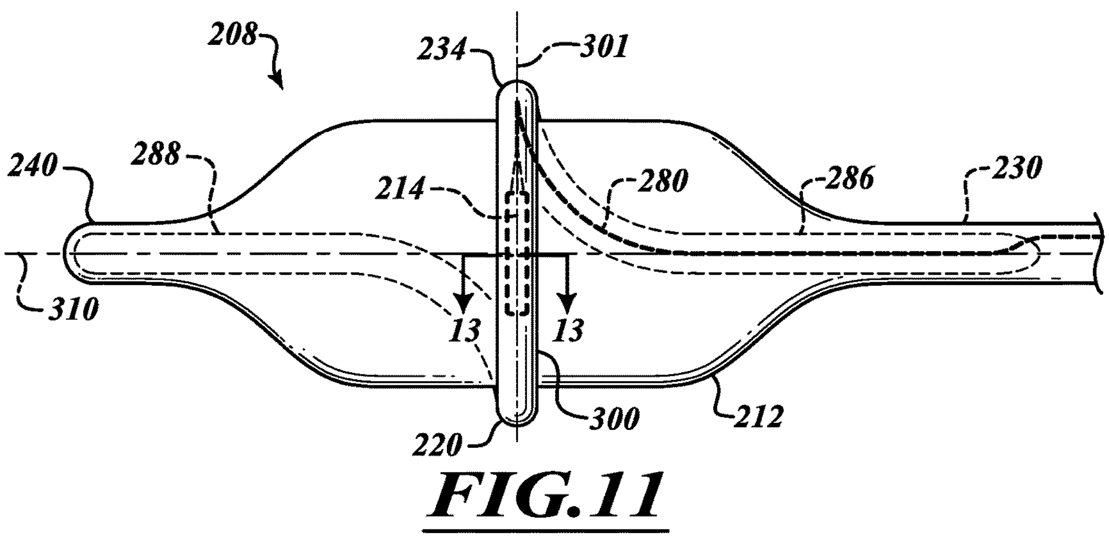
FIG. 11 is an elevational view of a left side of an ablation assembly.
Figure 12:
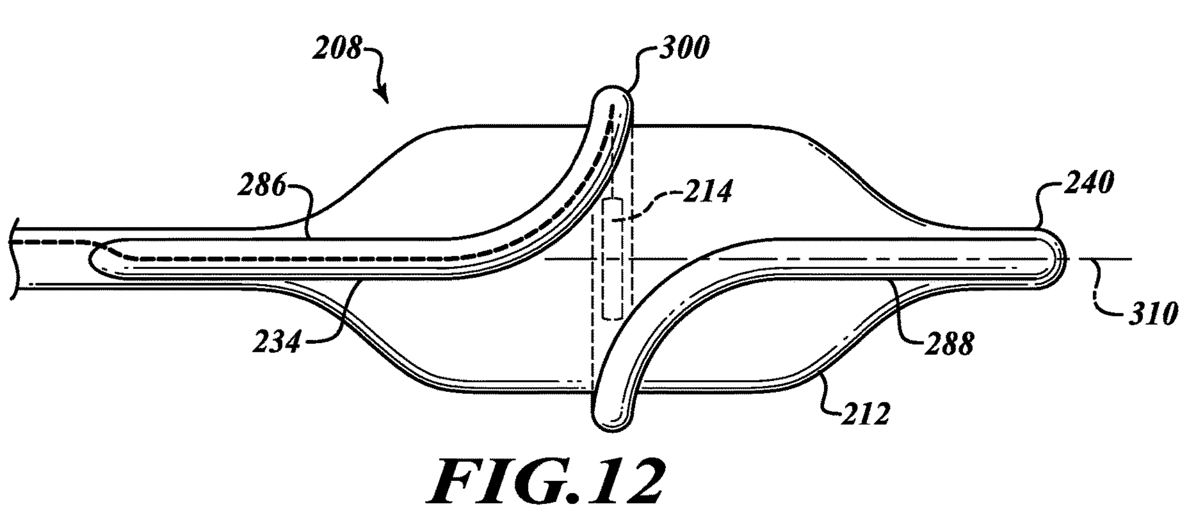
FIG. 12 is an elevational view of a right side of the ablation assembly of FIG. 11.

Referring to FIGS. 10-12 in which the ablation assembly 208 is in an expanded configuration, the conduit 234 surrounds and protects the electrode 214 and the power line 280 from the external environment and from external forces which could cause connection failure. The electrical connections are also not exposed to bodily fluids. The power line 380 can be routed along other fluid paths, if needed or desired. Alternatively, electrode 214 may be a metallic tubular member with conduit 234 being coupled to each of its ends in order to deliver coolant through the electrode 214. In this case, electrode 214 has an exposed external surface which is used to contact the airway wall during energy delivery.

The conduit 234 includes a proximal section 286, a distal section 288, and a non-linear section 300. The proximal section 286 functions as an inlet and extends distally from the elongate shaft 230. The non-linear section 300 extends circumferentially about the balloon 212 and has an arc length in a range of about 180 degrees to 450 degrees. As shown in FIG. 11, in the expanded configuration of ablation assembly 208, at least a portion of the non-linear section 300 can be positioned along an imaginary plane 301 that is approximately perpendicular to a longitudinal axis 310 of the inflated balloon 212 (and catheter shaft 230). The distal section 288 is aligned with the proximal section 286 and functions as an outlet and extends distally to the atraumatic tip 240.

When deflated (i.e., when not pressurized with coolant), the conduit 234 can be highly flexible to conform about the elongate shaft 230 and can be made, in whole or in part, of a material that assumes a preset shape when pressurized or activated. Such materials include, without limitation, thermoformed polymers (e.g., polyethylene terephthalate, polyethylene, or polyurethanes), shape memory materials, or combinations thereof. When the conduit 234 is inflated, it assumes a preset shape configured to position electrode 214 in the desired transverse orientation with respect to longitudinal axis 310.

The balloon 212 can be made, in whole or in part, of polymers, plastics, silicon, rubber, polyethylene, polyvinyl chloride, chemically inert materials, non-toxic materials, electrically insulating materials, combinations thereof, or the like. To enhance heat transfer, the balloon sidewall can comprise one or more conductive materials with a high thermal conductivity. For example, conductive strips (e.g., metal strips) can extend along the balloon 212 to help conduct thermal energy away from hot spots, if any. The balloon 212 can conform to irregularities on the airway surface (e.g., cartilaginous rings, side branches, etc.) and can be made, in whole or in part, of a distensible material, such as polyurethane (e.g., low durometer polyurethane) or other type of highly conformable material that may be transparent, semi-transparent, or opaque. The balloon 212 can have different inflated shapes, including a hot dog shape, an ovoid shape, a cylindrical shape, or the like.

Figure 13:
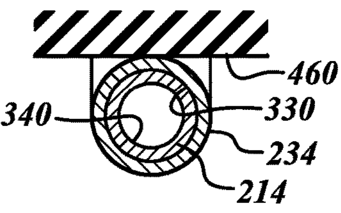
FIG. 13 is a cross-sectional view taken along a line 13-13 of FIG. 11.

FIG. 13 shows the electrode 214 positioned in a channel 330 of the conduit 234 and includes a coolant channel 340. The electrode main body 350 can be a rigid tube made, in whole or in part, of metal (e.g., titanium 304, stainless steel, or the like) or other suitable metal. In some embodiments, conduit 234 does not extend over the entire electrode 214, leaving a central portion of the tubular electrode exposed for direct contact with the airway wall. In other embodiments, the electrode main body 350 is made, in whole or in part, of a shape memory material. Shape memory materials include, for example, shape memory metals or alloys (e.g., Nitinol), shape memory polymers, ferromagnetic materials, combinations thereof, and the like. These materials can assume predefined shapes when released from a constrained condition or different configurations when activated with heat. In some embodiments, the shape memory material can be transformed from a first preset configuration to a second preset configuration when activated (e.g., thermally activated).

Figure 14:
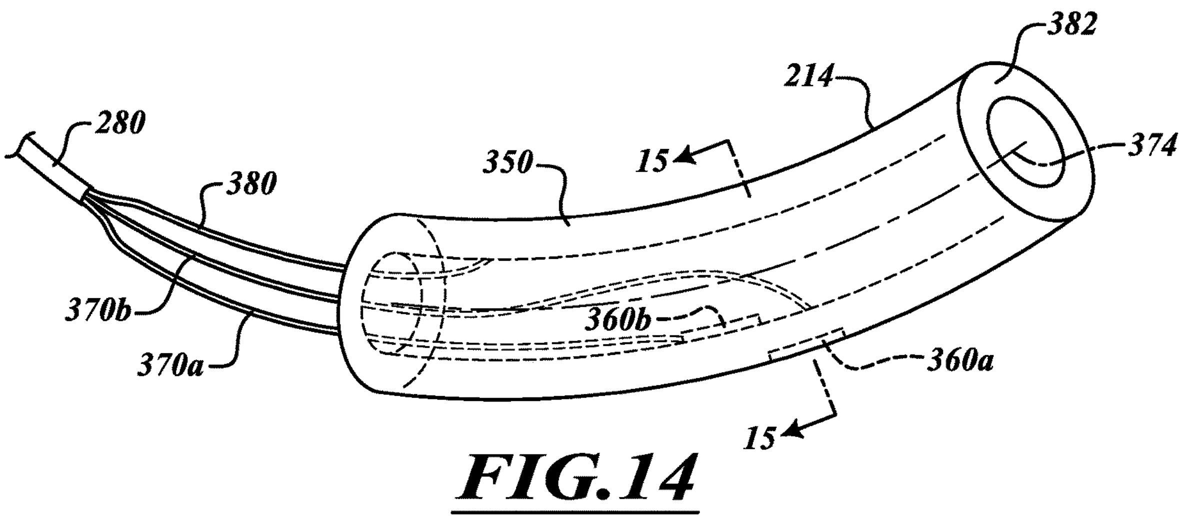
FIG. 14 is an isometric view of an electrode assembly.
Figure 15:
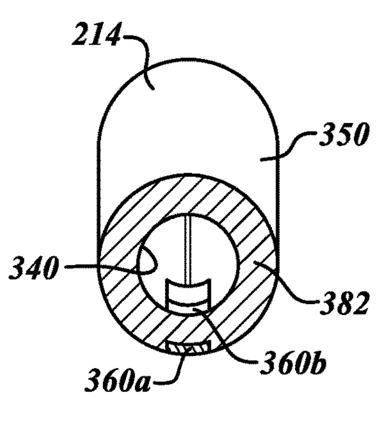
FIG. 15 is a cross-sectional view of the electrode assembly of FIG. 14 taken along a line 15-15.

As shown in FIGS. 14 and 15, sensors 360*a*, 360*b* (collectively "360") are coupled to the electrode main body 350. A pair of lines 370*a*, 370*b* (collectively "370") pass through the channel 340 and are coupled to the sensors 360*a*, 360*b*, respectively. In some embodiments, the sensor 360*a* is a contact sensor, and the sensor 360*b* is a temperature sensor and/or a pressure sensor. The number, positions, and types of sensors can be selected based on the treatment to be performed.

In multilayer embodiments, the electrode main body 350 can include at least one tube (e.g., a non-metal tube, a plastic tube, etc.) with one or more films or coatings. The films or coatings can be made of metal, conductive polymers, or other suitable materials formed by a deposition process (e.g., a metal deposition process), coating process, etc., and can comprise, in whole or in part, silver ink, silver epoxy, combinations thereof, or the like.

Radio-opaque markers or other types of visualization features can be used to position the main body 350. To increase visibility of the electrode 214 itself, the electrode 214 may be made, in whole or in part, of radiographically opaque material.

Figure 16:
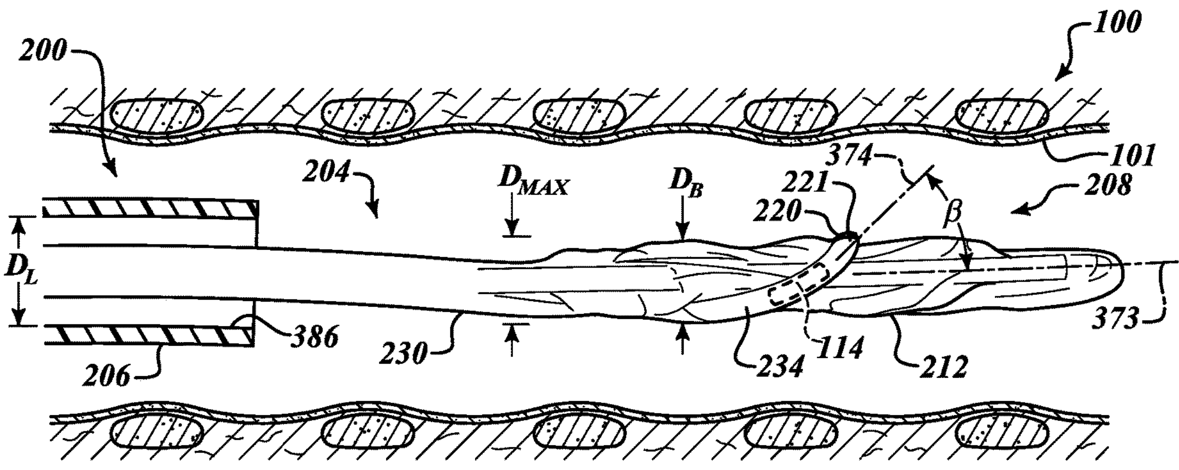
FIG. 16 is a partial cross-sectional view of a treatment system with a delivery device extending out of an apparatus.
Figure 17:
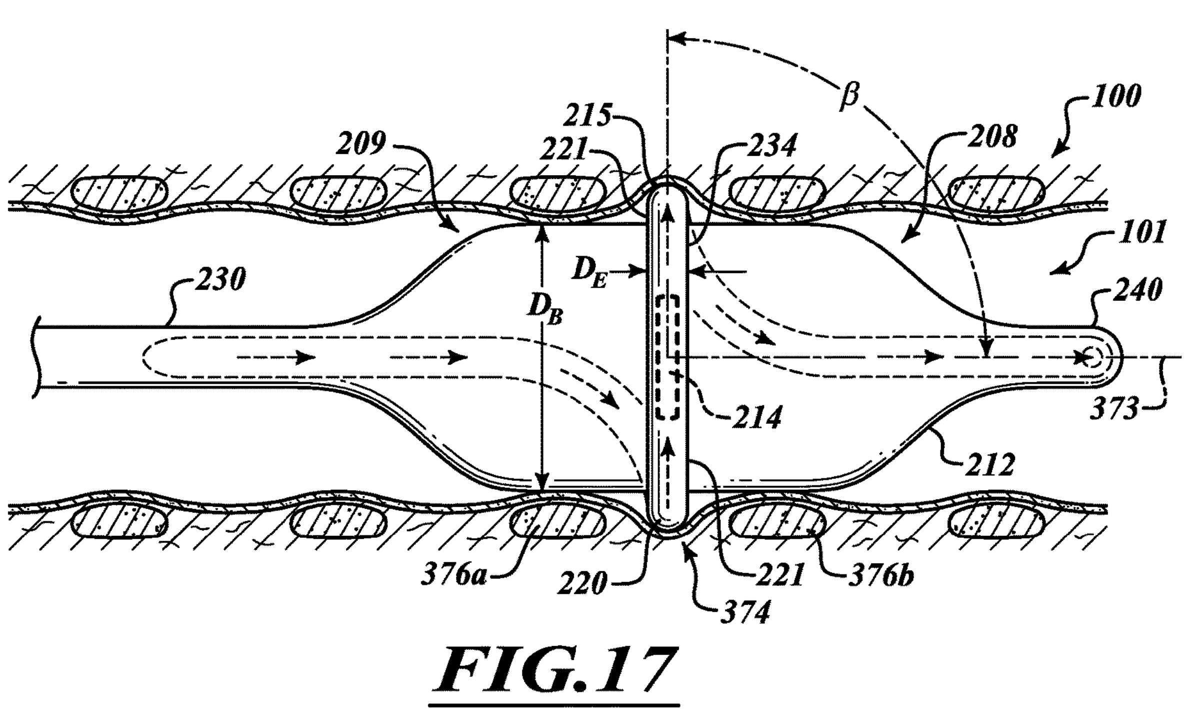
FIG. 17 is a side elevational view of a deployed ablation assembly with fluid flowing through an energy emitter assembly.
Figure 18:
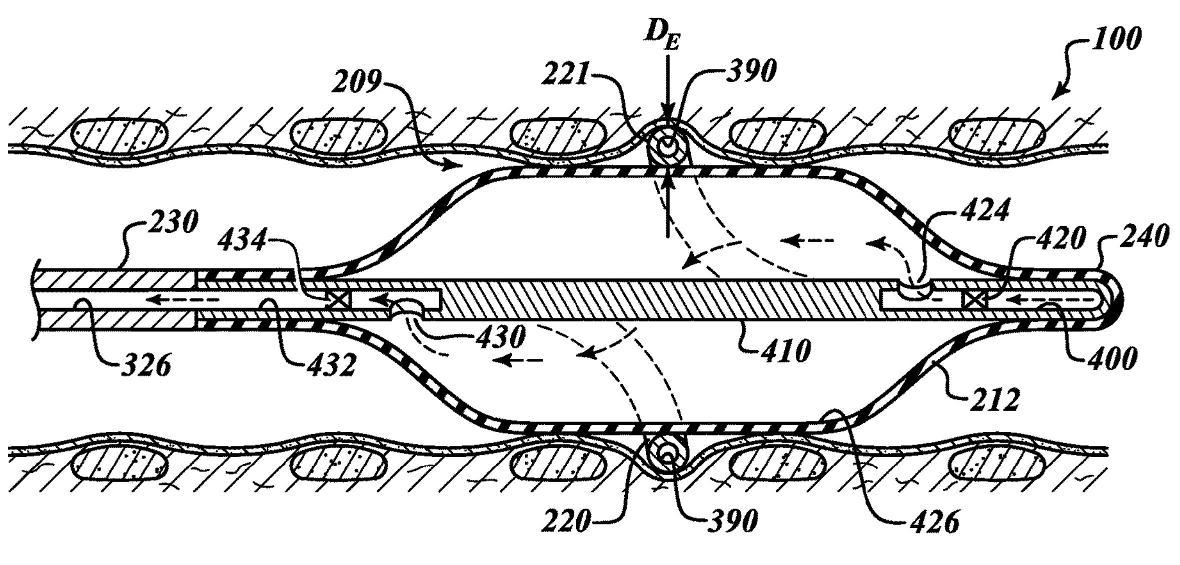
FIG. 18 is a cross-sectional view of the deployed ablation assembly with fluid flowing through an expandable member.

FIGS. 16-18 show one exemplary method of using the treatment system 200. A physician can visually inspect the airway 100 using the delivery apparatus 206 to locate and evaluate the treatment site(s) and non-targeted tissues before, during, and/or after performing a therapy. The delivery apparatus 206 can be a guide tube, a delivery sheath, a bronchoscope, or an endoscope and can include one or more viewing devices, such as optical viewing devices (e.g., cameras), optical trains (e.g., a set of lens), and the like. For example, the delivery apparatus 206 can be a bronchoscope having one or more lights for illumination and optical fibers for transmitting images. The catheter 207 may be adapted to be delivered over a guidewire (not shown) that passes between the balloon 212 and the energy emitter assembly 220. This provides for rapid exchange capabilities.

When the delivery apparatus 206 of FIG. 16 is moved along a body lumen 101 (e.g., airway), the collapsed ablation assembly 208 is held within a working channel 386 of the delivery apparatus 206. The conduit 234 can form a loop 221 such that the electrode 214 is almost parallel to a long axis 373 when the catheter 207 is in a substantially straight configuration. In the illustrated embodiment of FIG. 16, an angle β is defined between the direction of the long axis 373 of the catheter 207 and a long axis 374 of the electrode 214. The angle β can be in a range of about 0 degrees to about 30 degrees. In some embodiment, the angle β is in a range of about 0 degrees to about 20 degrees. The electrode 214, being curved, can also nest with and partially encircle the elongate shaft 230. In certain embodiments, at least a portion of the elongate shaft 230 is disposed within an arc of the electrode 214 for a further reduced profile. As such, the shaft 230 can be positioned between the ends of the electrode 214. Electrode 214 may have various lengths, depending on the desired length of the lesion to be created in each electrode position. In preferred embodiments, electrode 214 has a length of at least about 2 mm up to about 3 mm. The electrode can have a width (or diameter if cylindrical) no larger than the width of the spaces between the cartilage rings, preferably in some embodiments being 0.1 to about 3 mm.

With continued reference to FIG. 16, the diameter $D_L$ of the working channel 386 can be less than about 8 mm. The diameter $D_B$ of the deflated balloon 212 can be relatively small. For example, a minimum diameter $D_{B\ min}$ can be in a range of about 2 mm to about 3 mm, and a maximum diameter $D_{B\ max}$ in a range of about 5 mm to about 6 mm when the balloon 212 is fully collapsed. If the electrode 214 is collapsible, the diameter $D_{max}$ of the ablation assembly 208 can be less than about 3 mm. In ultra low-profile configurations, the maximum diameter $D_{max}$ can be less than about 2.8 mm.

The balloon 212 can be inflated to move the energy emitter assembly 220 near (e.g., proximate to or in contact with) the airway 100. The angle β can be increased between 70 degrees and about 110 degrees when the balloon 212 is fully inflated. FIG. 17 shows the ablation assembly 208 deployed, wherein the electrode 214 can be about perpendicular to the long axis 373. There can be play between the energy emitter assembly 220 and the balloon 212 such that the angle β is in a range of about 60 degrees to about 120 degrees in order to accommodate variations of anatomical structures, mis-alignment (e.g., mis-alignment of the catheter shaft 230), or the like. In some embodiments, the electrode 214 moves towards a circumferentially extending orientation as it moves from a delivery orientation to the deployed orientation. The electrode 214 in the deployed orientation extends substantially circumferentially along the wall of the airway 100. In certain embodiments, the electrode 214 will be configured to be positioned entirely within the spaces 374 between cartilage rings 376 along the airway wall when the ablation assembly 208 is in the fully deployed configuration.

FIGS. 17 and 18 show the energy emitter assembly 220 fluidically coupled to both the elongate shaft 230 and the balloon 212. Generally, coolant cools the tissue-contacting portion 215 of the energy emitter assembly 220. The cooling section 209 of the ablation assembly 208 contacts the airway wall 100 so as to cool tissue adjacent to the tissue-contacting portion 215 while energy is outputted by the electrode 214. The cooling section 209 can be formed by the portions of the energy emitting assembly 220 and the balloon 212 that contact the airway wall 100.

As the balloon 212 inflates, the electrode 214 moves (e.g., pivots, rotates, displaces, etc.) from a first orientation of FIG. 16 in which the electrode 214 extends axially along the airway 100 and a second orientation of FIG. 17 in which the entire electrode 214 is disposed in a space 374 between adjacent cartilage rings 376*a*, 376*b*. The balloon 212 can both cool the airway 100 and cause the electrode 114 to seat in the space 374.

FIG. 17 shows the energy emitter assembly 220 positioned to locate the electrode 214 in the space 374. In certain embodiments, the electrode 214, in the first orientation, extends a distance with respect to a longitudinal axis 373 (see FIG. 16) can be greater than the distance the electrode 214, in the second orientation, extends with respect to the longitudinal axis 373.

To deploy the energy emitting assembly 208, coolant from the elongate shaft 230 flows through the energy emitter assembly 220 and into the balloon 212. The electrode 214 can output a sufficient amount of energy to ablate a target region. The coolant absorbs thermal energy from electrode 214 and the airway wall 100.

The diameter $D_E$ of the electrode 214 and conduit 234 can be in a range of about 1.5 mm to about 2.5 mm when pressurized with coolant. Such embodiments are well suited to treat tissue outside the lung along the main bronchi. In certain embodiments, the diameter $D_E$ is about 2 mm. In yet other embodiments, the diameter $D_E$ can be in a range of about 0.1 mm to about 3 mm. The diameter $D_E$ of the deflated conduit 234 and electrode 214 can be about 0.1 mm to about 1 mm.

To treat a bronchial tree of a human, the diameter of the inflated balloon 212 can be in a range of about 12 mm to about 18 mm. For enhanced treatment flexibility, the inflated balloon diameter may be in a range of about 7 mm to about 25 mm. Of course, the balloon 212 can be other sizes to treat other organs or tissue of other animals.

The ablation assembly 208 provides differential cooling because the coolant in the energy emitter assembly 220 is at a lower temperature and higher velocity than the coolant in the balloon 212. Coolant, represented by arrows, flows out of the elongate shaft 230 and into the energy emitter assembly 220. The coolant proceeds through the energy emitter assembly 220 and the coolant channel 340 (FIG. 15) of the electrode 214. The coolant absorbs thermal energy from the electrode 214. The heated coolant flows into the tip 240 and proceeds proximally through a lumen 400, as shown in FIG. 18. The coolant flows through a valve 420 (e.g., a throttle) and passes through a port 424. The valve 420 is disposed along a fluid path connecting the energy emitting assembly 220 and the portion of the balloon 212 defining the cooling section 209. The coolant circulates in a chamber 426 and absorbs heat from the tissue. This helps keep shallow tissue below a temperature that would cause cell death or tissue damage.

The coolant flows through a port 430, a lumen 432, and a throttle 434. The throttles 420, 434 can cooperate to maintain a desired pressure. The throttle 420 is configured to maintain a first flow rate of the coolant through the energy emitting assembly 220 and a second flow rate of the coolant through the cooling section 209. The first flow rate can be significantly different from the second flow rate.

The conduit 234 can assume a preset shape when pressurized. The valves 420, 434 can cooperate to maintain the desired pressure within the balloon 212 within a range of about 5 psig to about 15 psig. Such pressures are well suited to help push the electrode 214 between cartilaginous rings. Other pressures can be selected based on the treatment to be performed. The valves 420, 434 can be throttle valves, butterfly valves, check valves, duck bill valves, one-way valves, or other suitable valves.

When RF energy is transmitted to the electrode 214, the electrode 214 outputs RF energy that travels through tissue. The RF energy can heat tissue (e.g., superficial and deep tissue) of the airway wall while the coolant cools the tissue (e.g., superficial tissues). The net effect of this superficial and deep heating by RF energy and superficial cooling by the circulating coolant is the concentration of heat in the outer layers of the airway wall 100, as discussed in connection with FIGS. 6 and 7. The temperature of the connective tissue can be higher than the temperatures of the epithelium, stroma, and/or smooth muscle. By example, the temperature of the connective tissue can be sufficiently high to cause damage to the nerve trunk tissue or other deep tissue while other non-targeted tissues of the airway are kept at a lower temperature to prevent or limit damage to the non-targeted tissues.

Heat can be concentrated in one or more of the internal layers (e.g., the stroma) of the airway wall or in the inner lining (e.g., the epithelium) of the airway wall. Furthermore, one or more of the vessels of the bronchial artery branches may be within the lesion. The heat generated using the electrode 214 can be controlled such that blood flowing through the bronchial artery branches protects those branches from thermal injury while nerve trunk tissue is damaged, even if the nerve tissue is next to the artery branches. The catheter 207 can produce relatively small regions of cell death. For example, a 2 mm to 3 mm section of tissue in the middle of the airway wall 100 or along the outer surface of the airway wall 100 can be destroyed. By the appropriate application of power and the appropriate cooling, lesions can be created at any desired depth.

A circumferential lesion can be formed around all or most of the circumference of the airway wall 100 by ablating tissue while slowly rotating the ablation assembly 208 or by positioning the ablation assembly 208 in a series of rotational positions at each of which energy is delivered for a desired time period. Some procedures form adjacent lesions that become contiguous and form a circumferential band all the way around the airway wall 100. In some embodiments, the entire loop 221 (FIG. 17) can be an electrode. The loop 221 can be coated with a conductive material and can carry the electrode. A single procedure can produce a circumferential lesion. After forming the lesion, coolant flowing into the balloon 212 can be stopped. The balloon 212 is deflated causing the energy emitter assembly 220 to recoil away from the airway wall 100. The catheter 207 may be repositioned to treat other locations or removed from the subject entirely.

Figure 19:
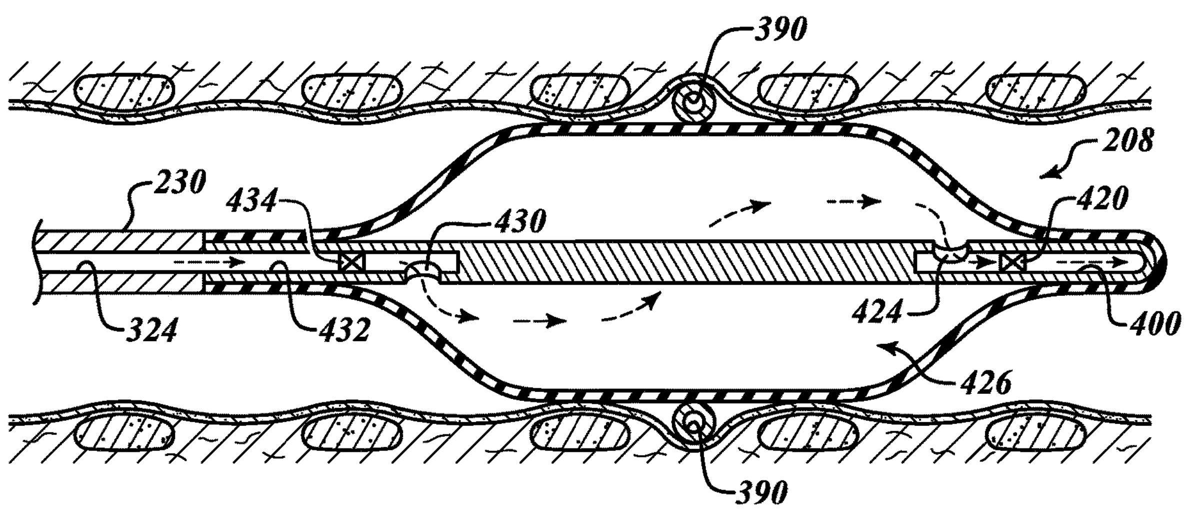
FIG. 19 is a cross-sectional view of the ablation assembly with fluid flowing into the expandable member.
Figure 20:
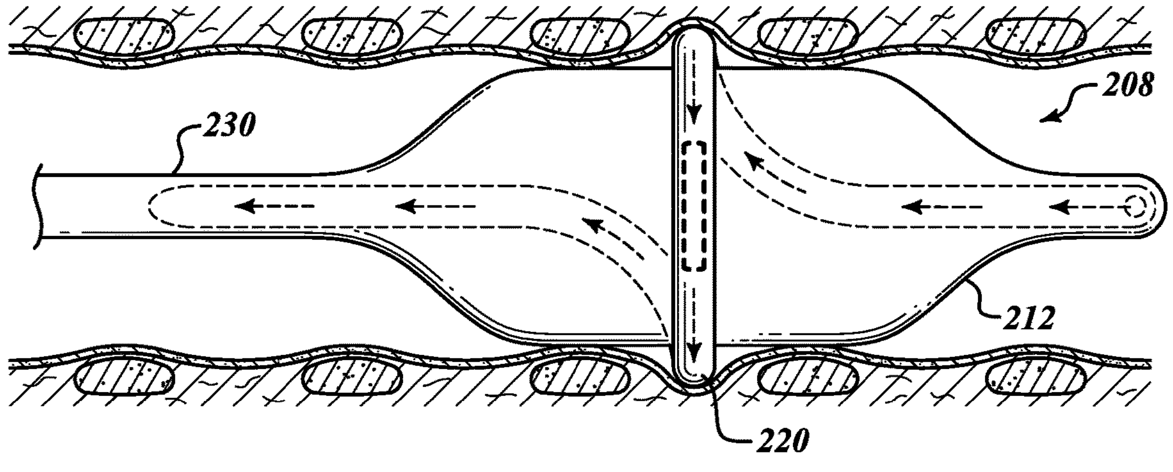
FIG. 20 is an elevational view of the ablation assembly with fluid flowing through the energy emitter assembly.

If the user wants the coolant in the balloon 212 to be at a lower temperature than the coolant in the energy emitter assembly 220, chilled coolant can be delivered into the balloon 212 and then into the energy emitter assembly 220. FIGS. 19 and 20 show such a coolant flow. Low temperature coolant flowing through the elongate body 230 passes through the valve 434 and the port 430. The coolant circulates in the chamber 426 and absorbs heat. The heated coolant flows through the valve 420 and proceeds through the energy emitter assembly 220 to cool the electrode 214.

Airway cartilage rings or cartilage layers typically have a significantly larger electrical resistance than airway soft tissue (e.g., smooth muscle or connective tissue). Airway cartilage impedes energy flow (e.g., electrical radiofrequency current flow) and makes the formation of therapeutic lesions with radiofrequency electrical energy to affect airway nerve trunk(s) challenging when the electrode is next to cartilage.

Figure 21:
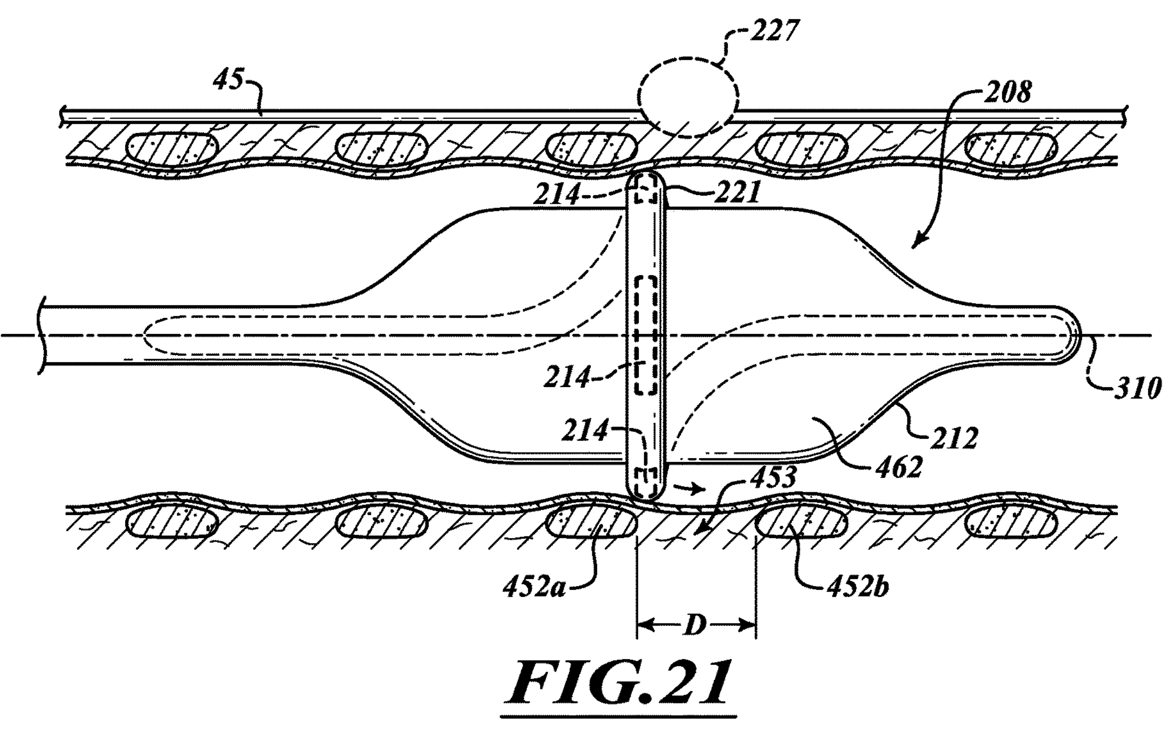
FIG. 21 is a side elevational view of an electrode adjacent a cartilaginous ring.
Figure 22:
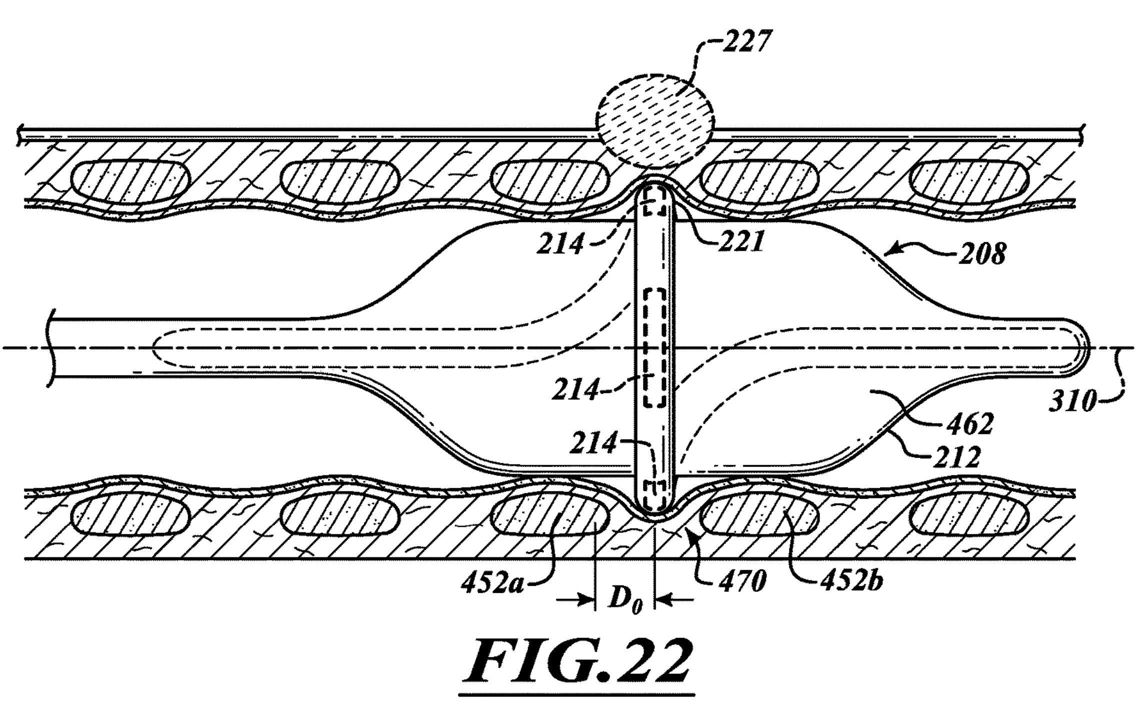
FIG. 22 is a side elevational view of electrodes positioned between cartilaginous rings.

Positioners can facilitate positioning of the electrodes. Such positioners include, without limitation, bumps, bulges, protrusions, ribs or other features that help preferentially seat the electrode 214 at a desired location, thus making it easy to perform the treatment or to verify correct positioning. FIGS. 21 and 22 show the energy emitter assembly capable of serving as an intracartilaginous positioner. When the balloon 212 presses against the airway 100, the loop 221 moves along the balloon 212 to preferentially position the electrodes 214 between cartilage rings 452*a*, 452*b*. The loop 221 protrudes outwardly from the balloon 212 a sufficient distance to ensure that the ablation assembly 208 applies sufficient pressure to the airway wall to cause self-seating. The catheter can be moved back and forth to help position the electrodes 214 next to soft compliant tissue 453 in the space 453. The energy emitter assembly 220 can be configured to displace a distance $D_o$ (e.g., measured along a long axis 310), which is at least half of the distance D between the cartilage rings 452*a*, 452*b*. This ensures that the electrodes 214 can be positioned generally midway between the cartilage rings 452*a*, 452*b*.

The plurality of electrodes 214 can reduce both treatment time and procedure complexity as compared to a catheter with a single electrode. This is because the multi-electrode catheter may have to be positioned a smaller number of times within a bronchial tree (or other hollow organ) as compared to single electrode catheters to produce a number of lesions of a desired therapeutic size. Multi-electrode catheters can thus precisely and accurately treat a user's respiratory system.

Figure 23:
FIG. 23 is a side elevational view of electrodes positioned between cartilaginous rings.
Figure 23:
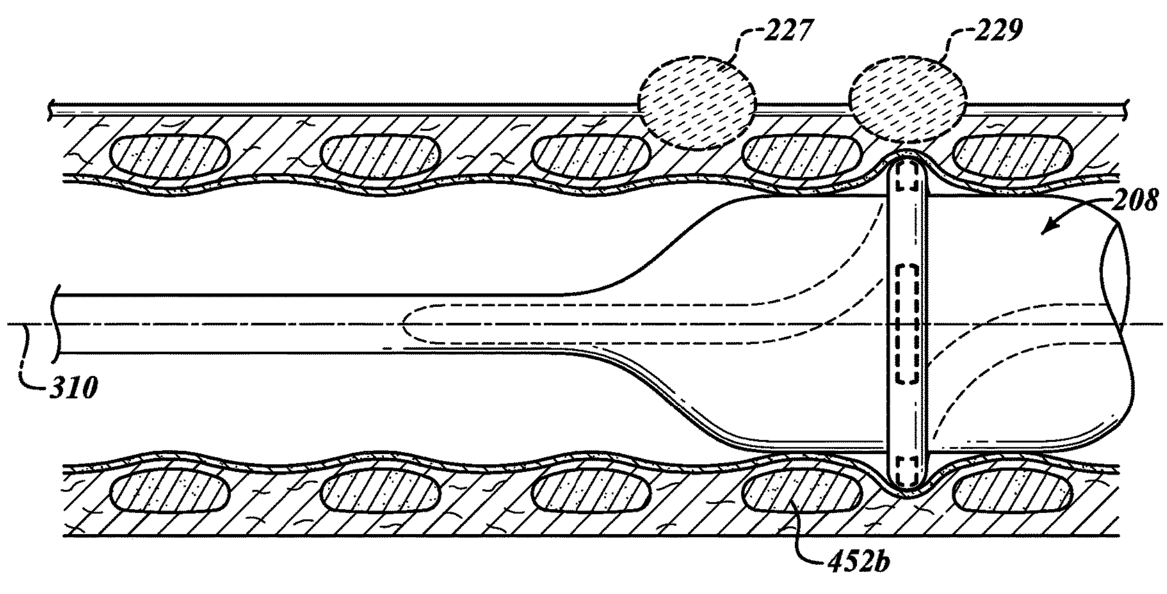

FIG. 21 shows a nerve 45 and a treatment region 227. Once the electrode 214 is seated between cartilage rings 452 the electrode 214 outputs energy to produce a lesion 22 in FIG. 22. The ablation assembly 208 can be moved to form a second lesion 229 of FIG. 23. Any number of scars can be formed distally or proximally to the lesion 227. In the illustrated embodiment, one cartilage ring 452*b* is between the scars 227, 229, but any number of cartilage rings can be positioned between lesions. The lesions 227, 229 make it difficult for axons to regrow and establish functional recovery.

Figure 24:
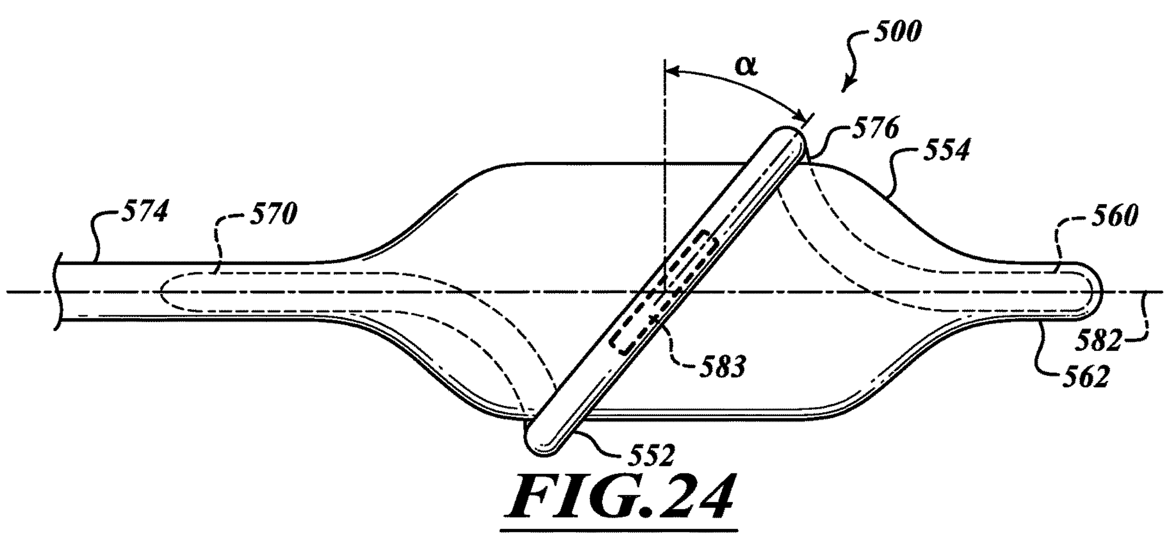
FIG. 24 is a side elevational view of the ablation assembly in an inflated state.

FIG. 24 shows an electrode oriented to form a lesion with a longitudinal length that is non-perpendicular relative to a longitudinal axis of a nerve fiber or trunk. An angle $\alpha$ is defined by a length of an electrode 583 and a longitudinal axis 582 of an ablation assembly 500. The angle $\alpha$ is less than 90° and, in some embodiments, is in a range of about 45° to about 80°.

Figure 24A:
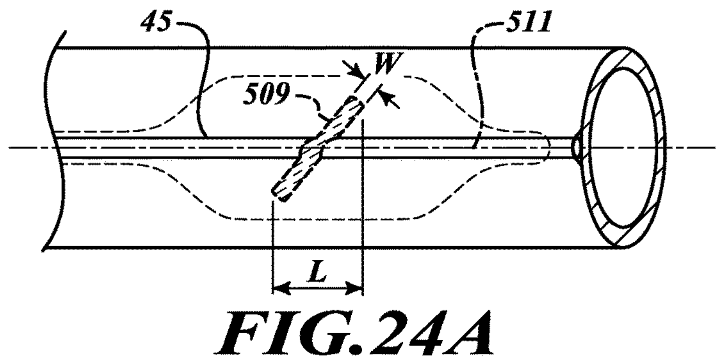
FIG. 24A is an elevational view of a lesion along a nerve trunk of an airway generated using the ablation assembly of FIG. 24.

FIG. 24A shows a lesion 509 along a nerve trunk 45 formed using the ablation assembly 500 of FIG. 24. A length L of the lesion 509 in the direction of the longitudinal axis 511 of the nerve fiber 45 is significantly greater than a width W of the lesion 509. Accordingly, the angle $\alpha$ can be selected to determine the length of nerve fiber 45 that is damaged. The angle $\alpha$ can be increased or decreased to increase or decrease the length the lesion 509 extends along the trunk 45.

Figure 25:
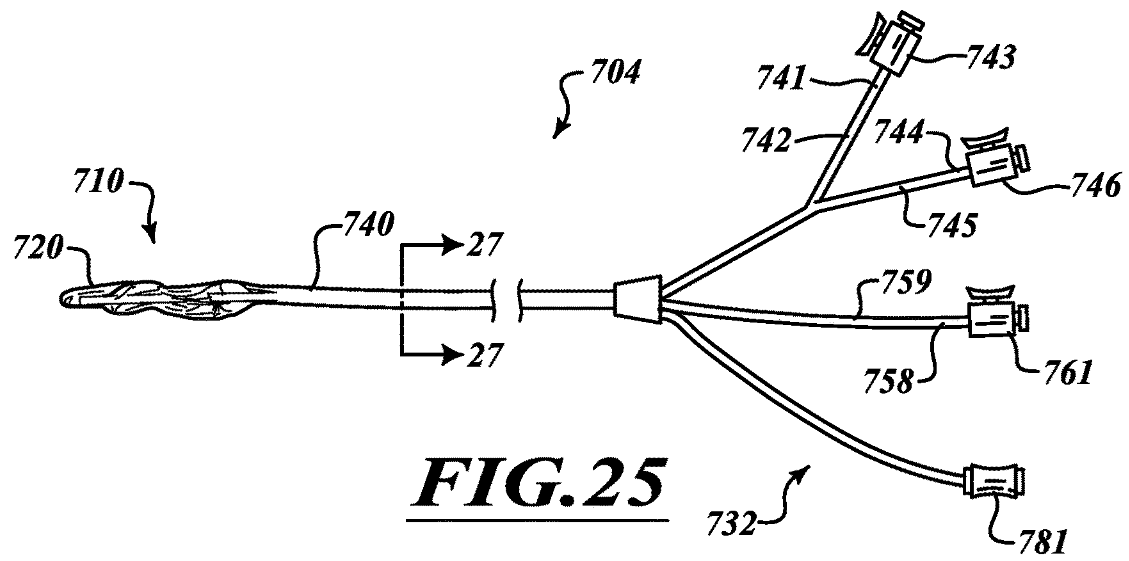
FIG. 25 is a side elevational view of a delivery device.
Figure 26:
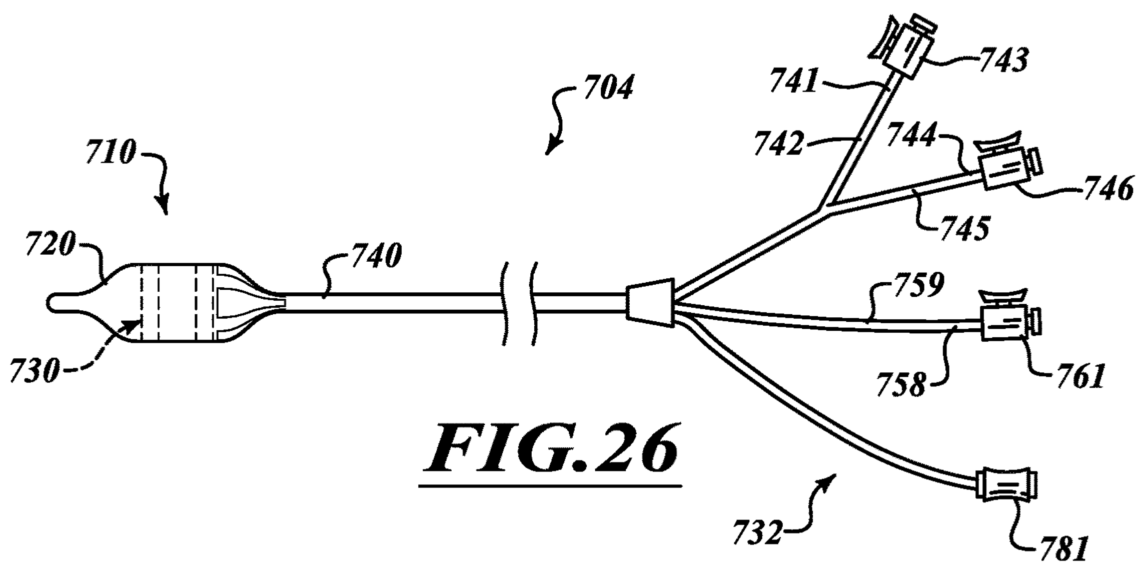
FIG. 26 is a side elevational view of the delivery device of FIG. 25 with a deployed expandable element.

FIGS. 25 and 26 show an ablation assembly 710 including an inflatable balloon 720 and an energy emitter assembly 730 (shown in dashed line in FIG. 25). Separate channels provide separate fluid paths to independently adjust the pressure in the balloon 720 and energy emitter assembly 730. Both the balloon 720 and the energy emitter assembly 730 can be made of a compliant material (e.g., urethane or other compliant biocompatible material) to fit in differently sized bronchial lumens. Advantageously, fewer catheter stock keeping units (SKUs) can be required compared to catheter balloons made from non-compliant materials, which are not optimally adjustable for fitting in different sized lumens.

The catheter 704 has a proximal section 732 configured for differential cooling. A proximal end 741 of an inflow line 742 has an inline valve 743 and is in fluid communication with an inflow lumen 750 of FIG. 27. A feed conduit 816 of FIG. 29 delivers coolant from the inflow lumen 750 to a chamber 811 of the inflation assembly 780*a*.

Figure 27:
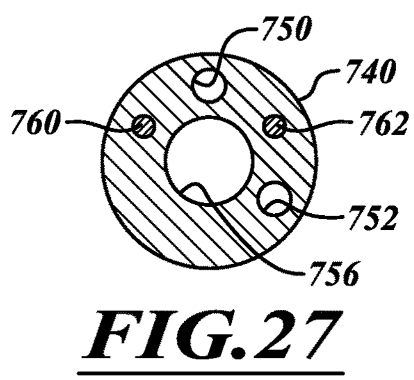
FIG. 27 is a cross-sectional view of an elongate body taken along a line 37-37 of FIG. 35.
Figure 30:
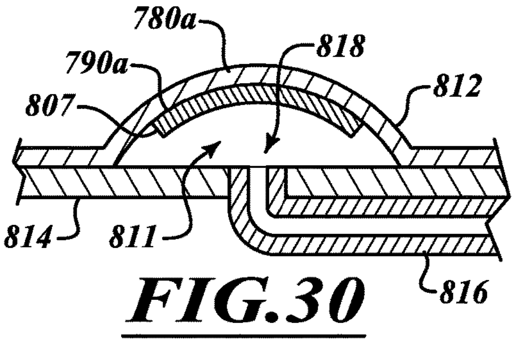
FIGS. 30 and 30A are detailed views of an electrode assembly of FIG. 30.
Figure 30A:
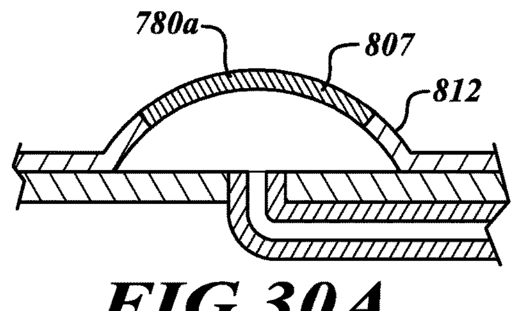

A proximal end 744 of an inflow line 745 of FIG. 25 has an inline valve 746 and is in fluid communication with an inflow lumen 752 of FIG. 27. The inline valves 743, 746 can be connected to fluid supplies. A proximal end 758 of an outflow line 759 has an outline valve 761 and is in fluid communication with an outflow lumen 756 of FIG. 35. Power lines 760, 762 separately couple electrodes 790*a*, 790*b* respectively to a power source connector 781. An electrode 807 is coupled to a conductive wall 812 that defines the channel 812. FIG. 30A shows the electrode 807 for direct tissue contact.

Figure 28:
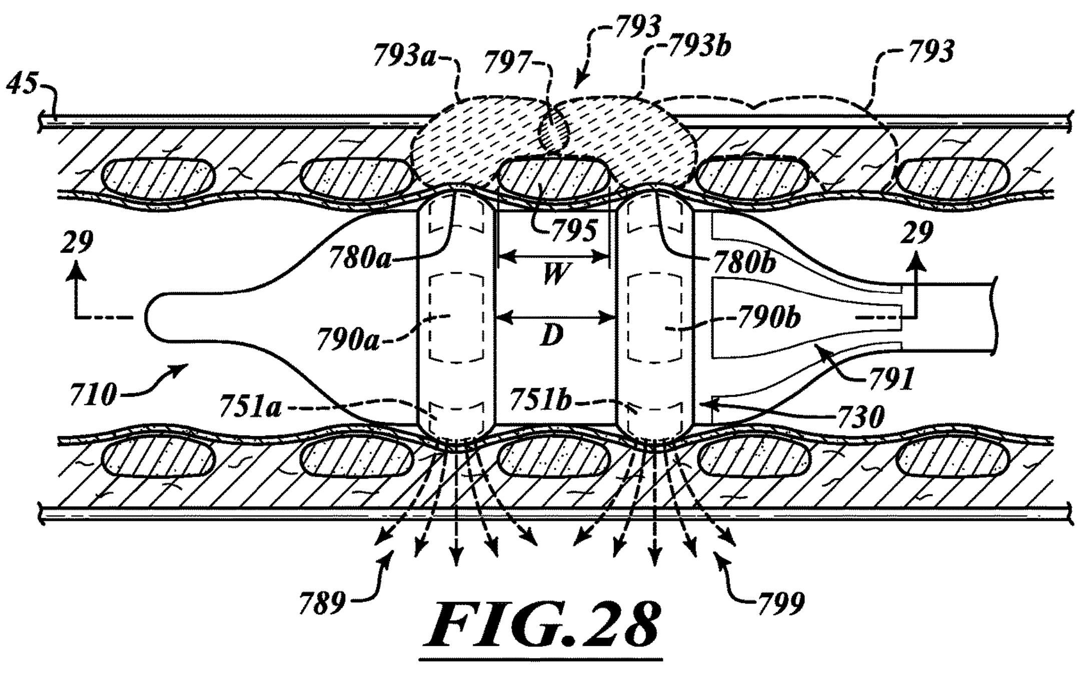
FIG. 28 is a side elevational view of an ablation assembly with inflated electrode assemblies.
Figure 29:
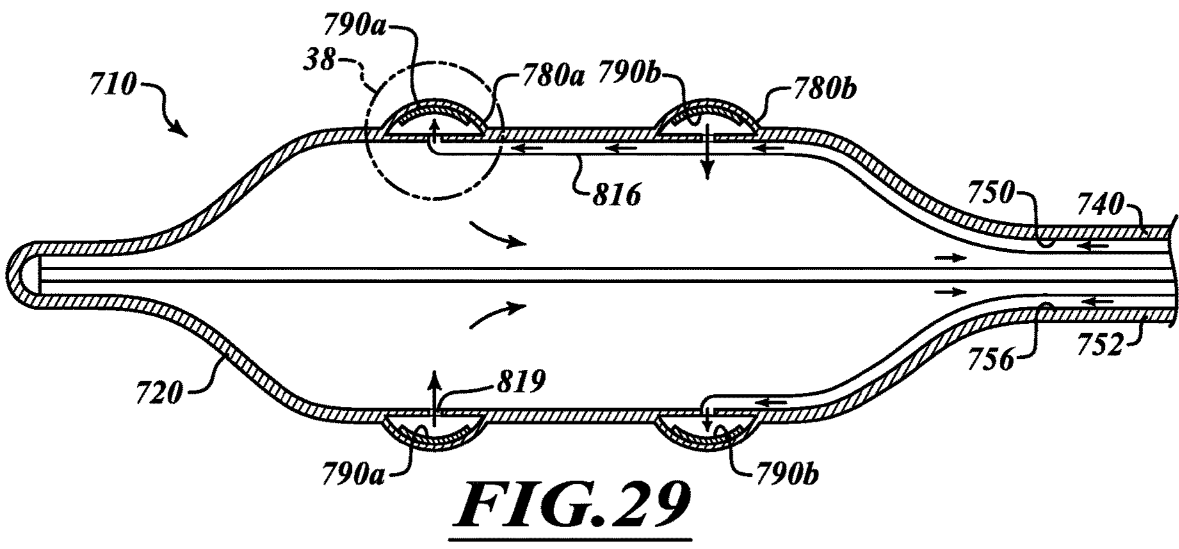
FIG. 29 is a cross-sectional view of the ablation assemblies of FIG. 28 taken along a line 29-29.

FIGS. 28 and 29 show inflatable ablation assemblies 780*a*, 780*b* (collectively "780") in an expanded state. The assemblies 780 can be independently inflated to help position electrodes 790*a*, 790*b*. Different coolants (e.g., saline, water, or the like) at different coolant temperatures (e.g., iced, warmed, room temperature, etc.) can flow through the ablation assemblies 780. The inflation pressure can be increased to increase the force applied to an airway wall and to help seat the ablation assemblies 780.

The ablation assemblies 780 may be spaced apart to allow each of the ablation assemblies 780 to be positioned between cartilaginous rings. For example, the distance D in FIG. 36 can be in a range of about 1 mm to about 5 mm. A physician can determine the distance D by inspecting an airway and can then select an appropriately sized catheter. In addition to being axially spaced apart, electrodes 790*a*, 790*b* may be disposed in circumferentially offset positions so as to deliver energy to different facets of the airway wall. For example, electrode 790*a* may be offset by 45 degrees, 90 degrees, or 180 degrees relative to electrode 790*b*. Further, each ablation assembly 780*a*, 780*b* may have multiple electrodes spaced circumferentially around balloon 720.

Fluids at different temperatures can be delivered to the ablation assemblies 780 and the balloon 720. In some embodiments, the coolant is delivered through cooling channels of the energy emitting assemblies 780 and then into the balloon 720 if the therapeutic goal is to produce lesions with the maximum depth. The balloon 720 and the energy emitting assemblies 780 can also be coupled to a common source (or sink) path. This allows for unique coolant flow in each path. This also may reduce the overall diameter of the expanded ablation assembly 710 as compared to using completely separate coolant paths. Electrodes 780*a*, 780*b* may be independently controlled so that energy may be delivered simultaneously or separately, and at the same or different power levels.

In monopolar mode, the energy emitting assemblies 780*a*, 780*b* can be operated simultaneously or sequentially. For monopolar embodiments, an external electrode pad can be placed on the skin of the subject to ensure that the lesion is formed at the desired location. Alternatively, an internal electrode can be placed in the subject to ensure that a lesion is formed in a desired location. In a bipolar mode, RF energy is transferred between the electrode assemblies 780*a*, 780*b*.

As shown in FIG. 28, the energy ablation assemblies 780*a*, 780*b* can cooperate to form a lesion 793 that extends around the outer side of a cartilage ring 795. The length of the lesion 793 along the nerve trunk 45 is greater than a width W of the cartilage ring 795. To form the lesion 793, energy ablation assemblies 780*a*, 780*b* can operate in bipolar mode. Alternatively, the energy emitter 780*a* can form a first lesion 793*a* and subsequently the energy emitter 780*b* can form the other lesion 793*b*.

An overlapping region 797 can receive a higher energy density than the first lesion 793*a* and/or the second lesion 793*b*, resulting in a higher degree of injury in the overlapping region. The length of the composite lesion 793 can be in a range of about 1 mm to 10 mm. The dimension of the lesion can be increased to further inhibit reinnervation. Accordingly, other dimensions are also possible, if needed or desired.

The ablation assembly 710 can be moved to form additional lesions along the airway. By way of example, the lesion 793, illustrated in phantom line, can be produced to have a composite lesion that extends across two cartilage rings. In other embodiments, energy emitting assemblies 780*a*, 780*b* can be sufficiently spaced apart to allow at least two cartilage rings therebetween to produce spaced apart lesions.

FIG. 28 shows a current density, represented by arrows 789, 799, from lower electrodes 751*a*, 751*b* is higher in tissue located generally between the cartilage rings. The density of the scar in the high current region would be greater than the density in the low density region.

Figure 31:
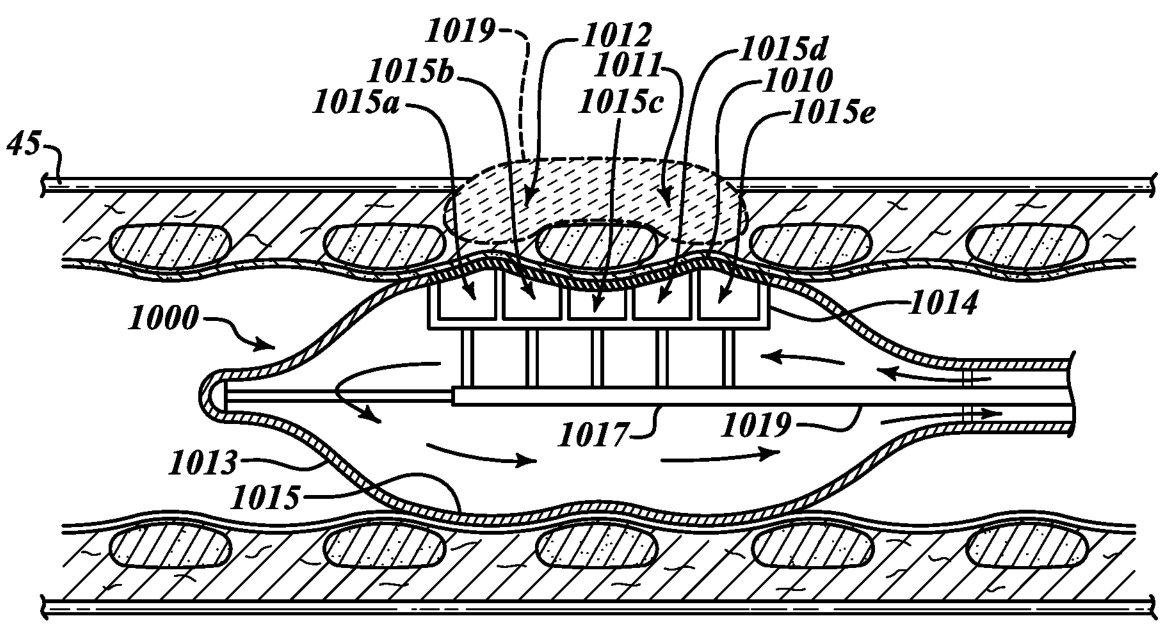
FIG. 31 is a cross-sectional view of an ablation assembly with addressable electrode cooling device.

FIG. 31 shows an energy emitting assembly 1000 that includes an electrode 1010 dimensioned to extend across intracartilaginous spaces 1011, 1012. An electrode cooling device 1014 includes cooling channels 1015*a*-1015*e*. A manifold 1017 delivers coolant to the channels 1015*a-e*. A multi-lumen shaft 1019 can deliver fluids to the manifold 1017. The same coolant can be delivered through each of the channels 1015. In other embodiments, fluids at different temperatures can be delivered independently through the channels 1015*a-e*. The lesion 1019, illustrated in phantom line, extends along a nerve trunk 45 and, in some embodiments, inwardly into intracartilaginous spaces.

The electrode 1010 can comprise a plurality of independently controlled electrodes, if needed or desired. An inflatable member 1013 may be cooled using a coolant circulating in an internal chamber 1015. In some procedures, room temperature fluid (e.g., saline) can be used to inflate the inflatable member 1013 to move the electrode 1010 into contact with a side of the airway. Localized cooling can be achieved using the electrode cooling device 1014.

Figure 32:
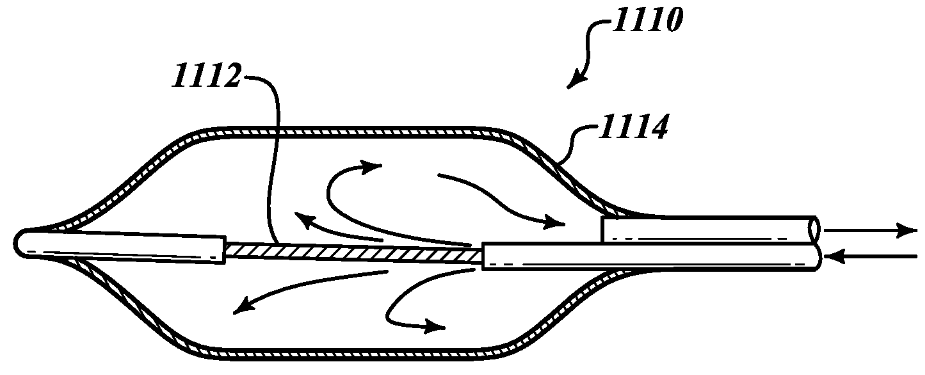
FIG. 32 is a cross-sectional view of an ablation assembly for outputting microwave energy.

FIG. 32 shows an ablation assembly 1110 that includes an antenna 1112 (e.g., a microwave antenna) that outputs energy to generate a relatively long region. Coolant flows through an inflatable member 1114 to cool tissue. The microwave antenna 1112 can deliver microwave energy so as to alter nerve tissue in a manner which disrupts transmission of nerve signals while non-target tissue disposed between the microwave antenna 1112 and the targeted tissue. In one exemplary embodiment, an antenna that may be particularly effective in pulmonary applications for microwave energy delivery is a multi-slot coaxial design to provide a desired specific absorption rate (SAR) pattern. Specific absorption rate, or SAR, is a proxy for energy delivery to the tissue, or heating profiles of the tissue, and are the standard way in which antenna designs are evaluated and optimized. The SAR can be selected to achieve desired lesion size, density, spacing, or the like.

Optionally, shielding can be provided on one or more sides of the device to further focus the microwave energy into the tissue and/or to protect non-target tissues. Shielding can be metallic foil, metal loaded polymer, metallic mesh with mesh opening of an appropriate fraction of the wavelength in use so as to block transmission of the waves therethrough, or any known microwave shielding material. This system can take any of the forms previously disclosed. U.S. application Ser. No. 13/081,406 discloses antennas, treatment routines, and the like can be performed to create the lesions disclosed herein. U.S. application Ser. No. 13/081,406 is incorporated by reference in its entirety.

FIGS. 33 and 34 show an ablation assembly 800 with a deployment catheter 811 having a balloon 810 and an energy emitter assembly 820 removably positionable over the balloon 810. Energy emitter assembly 820 comprises a pair of tubular shafts 817, 819 connected by a distal loop 823. Distal loop 823 may be pre-formed around an axis parallel to the longitudinal axes of the shafts 817, 819. Alternatively the distal loop 823 can be configured to assume the deployed orientation when pressurized by the introduction of coolant in shafts 817, 819.

One of shafts 817, 819 is adapted to deliver coolant through loop 823 while the other received coolant from the loop and returns it to the proximal end of the device. In FIG. 35, the shaft 817 delivers coolant to the balloon 810. The coolant exits the balloon 810 via the shaft 819. As shown in FIG. 34, a distal tip 834 of deployment catheter 811 can be inserted and passed through a receiving opening 830 of the energy emitter assembly 820. Once an electrode, illustrated as a surface mounted electrode 836, is positioned between the distal tip 834 and a proximal end 840 of the balloon 810, the balloon 810 is inflated to snugly hold the energy emitter assembly 820.

The energy emitter assembly 820 can be moveable between a straightened and collapsed configuration for delivery and the illustrated deployed configuration. For example, in the preshaped embodiment described above, the distal loop 823 on energy emitter assembly 820 can be straightened and collapsed inwardly so as to be positionable in a constraining sheath during introduction. Upon removal from the sheath, distal loop 823 will return to its unbiased deployed orientation, lying in a plane generally perpendicular to the longitudinal axes of shafts 817, 819. In alternative embodiments, the distal loop 823 may be flaccid and collapsible when unpressurized, and will assume the desired deployed shape when coolant is introduced through shafts 817, 819. To manufacture distal loop 823, a polymer tube may be heat treated to assume a desired shape when pressurized.

By decoupling the energy emitter apparatus 820 from the deployment catheter 811 they may be introduced separately from each other, allowing the apparatus to be introduced through very small-diameter passageways. This is particularly useful to allow the ablation assembly to be inserted through a working channel of a bronchoscope. First, the energy emitter assembly 820 may be collapsed and introduced through the working channel (with or without a sheath), then the deployment catheter 811 may be introduced. The combined apparatus may then be assembled within the airway outside the working channel.

As shown in FIGS. 35 and 36, fluids can be independently delivered through the energy emitter assembly 820 and the balloon 810. FIG. 35 shows arrows representing coolant flowing through the energy emitter assembly 820. FIG. 36 shows arrows representing coolant flowing through the balloon 810. The coolant can flow through a delivery lumen 854 and a port 856. The coolant exits a chamber 857 via a port 860 and flows through a return lumen 864. A separate delivery lumen 867 delivers coolant to the energy emitter assembly 820. A return lumen 869 delivers the coolant out of the energy emitter assembly 820. In some embodiments, coolants are independently delivered to the balloon 810 and the energy emitter assembly 820. Separate lines can be connected to the balloon 810 and the energy emitter assembly 820.

One or move valves can provide for different flow rates through the balloon 810 and the energy emitter assembly 820. For example, a valve system (e.g., one or more valves, throttles, etc.) can provide a first flow rate of coolant through the energy emitting assembly 220 and a second flow rate of coolant through the balloon 810. The first flow rate can be significantly different from the second flow rate. For example, the first flow rate can be significantly greater than the second flow rate. In yet other embodiments, the first flow rate can be generally the same as the second flow rate.

Figure 37:
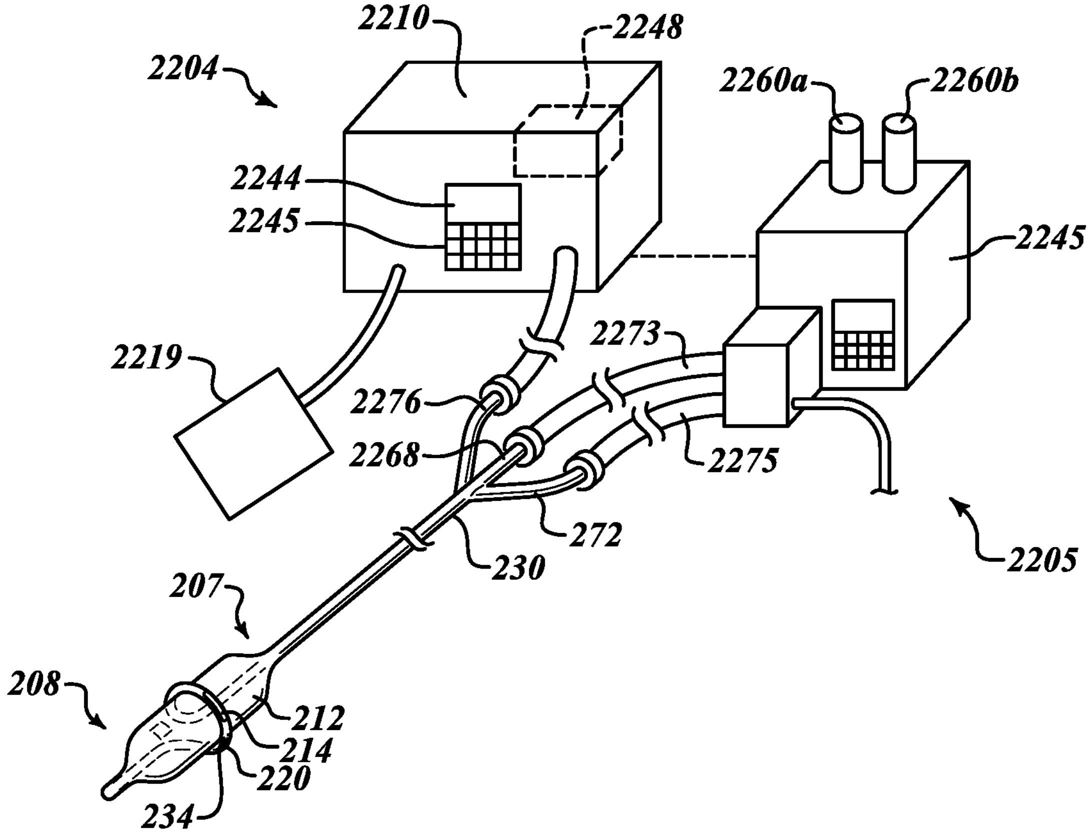
FIG. 37 is an isometric view of a treatment system.

FIG. 37 shows a treatment system 2204 that includes a media delivery system 2245 and a control module 2210 coupled to an elongate member in the form of a shaft 230 of a catheter 207. A temperature control device 2205 is coupled to the media delivery system 246. An electrode pad 2219 for placement against the patient is connected to the control module 2210.

The control module 2210 can include an energy generator, such as a radio frequency (RF) electrical generator. RF energy can be outputted at a desired frequency. Example frequencies include, without limitation, frequencies in a range of about 50 KHZ to about 1,000 MHZ. When the RF energy is directed into tissue, the energy is converted within the tissue into heat causing the temperature of the tissue to be in the range of about 40° C. to about 99° C. The RF energy can be applied for about 1 second to about 160 seconds. In some embodiments, the RF generator has a single channel and delivers approximately 1 to 25 watts of RF energy and possesses continuous flow capability. Other ranges of frequencies, time intervals, and power outputs can also be used. An internal power supply 2248 can be an energy storage device, such as one or more batteries. Electrical energy can be delivered to the energy emitter assembly 2220, which converts the electrical energy to RF energy or another suitable form of energy. Other forms of energy that may be delivered include, without limitation, microwave, ultrasound, direct current, or laser energy. Alternatively, cryogenic ablation may be utilized wherein a fluid at cryogenic temperatures is delivered through the shaft 230 to cool a cryogenic heat exchanger on the assembly 208.

The control module 2210 can also have one or more communication devices to wirelessly, optically, or otherwise communicate with the media delivery system 2245. Pumps of the media delivery system 2245 can be operated based on the signals. In other embodiments, the control module 2210 can include the media delivery system 2245. A single unit can therefore control operation of the catheter 207 and the temperature control device 2205.

The media delivery system 2245 can pump cooling media through the pulmonary treatment device 207 and the temperature control device 205 and includes a media container **2260*a* coupled to a supply line 268 and a media container 2260*b* coupled to a return line 272. Luer connectors or other types of connectors can couple the lines 268, 272 to lines 2273, 2275. The media container 2260*a* can include a container (e.g., a bottle, a canister, a tank, a bag, or other type of vessel for holding fluid or other media). In pressurizable embodiments, the media container 2260*a* includes one or more pressurization devices (e.g., one or more pumps, compressors, or the like) that pressurize coolant. Temperature control devices (e.g., Peltier devices, heat exchangers, or the like) can cool or recondition the fluid. The media can be a coolant including saline, deionized water, refrigerant, cryogenic fluid, gas, mixtures thereof, or the like. In other embodiments, the media container 2260*a* can be an insulated container that holds and delivers a chilled coolant to the supply line 268. In embodiments, the media container 2260*a*** is a bag, such as an IV type bag, configured to be held on a pole.

The delivery devices disclosed herein can treat the digestive system, nervous system, vascular system, or other systems. For example, treatment systems, elongate assemblies, intra-luminal catheters, and delivery devices disclosed herein can be delivered through the esophagus, intestines, and or stomach to treat the digestive system. Treatments system can target tissue within a vessel wall, tissue adjacent to vessel walls (e.g., tissue contacting a vessel wall), or tissue spaced apart from a vessel wall. The target tissue can be nerve tissue, tissue of a hollow vessel (e.g., a blood vessel, duct, or the like), cardiac tissue (e.g., tissue of a blood vessel, tissue forming a chamber of a heart, or the like), or vessels through which fluid flows. In certain embodiments, a treatment system can be positioned in one hollow vessel to injure another hollow vessel.

The treatment systems and its components disclosed herein can used as an adjunct during another medical procedure, such as minimally invasive procedures, open procedures, semi-open procedures, or other surgical procedures (e.g., lung volume reduction surgery) that provide access to a desired target site. Various surgical procedures on the chest may provide access to lung tissue, cardiovascular tissue, respiratory tissue, or the like. Access techniques and procedures used to provide access to a target region can be performed by a surgeon and/or a robotic system. Those skilled in the art recognize that there are many different ways that a target region can be accessed.

The delivery devices disclosed herein can be used with guidewires, delivery sheaths, optical instruments, introducers, trocars, biopsy needles, or other suitable medical equipment. If the target treatment site is at a distant location in the patient (e.g., a treatment site near the lung root 24 of FIG. 1), a wide range of instruments and techniques can be used to access the site. The flexible elongated assemblies can be easily positioned within the patient using, for example, steerable delivery devices, such as endoscopes and bronchoscopes, as discussed above.

Semi-rigid or rigid elongated assemblies can be delivered using trocars, access ports, rigid delivery sheaths using semi-open procedures, open procedures, or other delivery tools/procedures that provide a somewhat straight delivery path. Advantageously, the semi-rigid or rigid elongated assemblies can be sufficiently rigid to access and treat remote tissue, such as the vagus nerve, nerve branches, nerve fibers, and/or nerve trunks along the airways, without delivering the elongated assemblies through the airways. The embodiments and techniques disclosed herein can be used with other procedures, such as bronchial thermoplasty.

Unless the context requires otherwise, throughout the specification and claims which follow, the word "comprise" and variations thereof, such as "comprises" and "comprising" are to be construed in an open, inclusive sense, that is, as "including but not limited to."

The various embodiments described above can be combined to provide further embodiments. These and other changes can be made to the embodiments in light of the above-detailed description. The embodiments, features, systems, devices, materials, methods and techniques described herein may, in some embodiments, be similar to any one or more of the embodiments, features, systems, devices, materials, methods and techniques described in of PCT Application No. PCT/US2010/056424; U.S. application Ser. No. 12/463,304 filed on May 8, 2009; U.S. application Ser. No. 12/913,702 filed on Oct. 27, 2010; and U.S. application Ser. No. 13/081,406 filed on Apr. 6, 2011. Each of these applications is incorporated herein by reference in its entirety. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned PCT Application No. PCT/US2010/056424 and U.S. application Ser. Nos. 12/463,304; 12/913,702; and Ser. No. 13/081,406. For example, the apparatuses of disclosed in U.S. patent application Ser. No. 12/463,304 may incorporate the electrodes or other features disclosed herein. U.S. patent application Ser. No. 12/463,304 discloses devices for penetrating wall to deliver agents (e.g., scarring agents, gels, or the like) and mechanically injuring tissue. These devices can be used to create scar tissue at a target sites. U.S. patent application Ser. No. 12/913,702 discloses systems, devices, and methods of injuring tissue utilizing electrodes. Cryogenic energy can be used to perform cryogenic ablation, as described in U.S. application Ser. No. 13/081,406, because nerve tissue is more sensitive to cold than other types of tissue, such as connective tissue. In cryogenic ablation, a fluid at cryogenic temperatures can selectively damage nerve tissue while other tissue less sensitive to cold can be preserved. PCT Application No. PCT/US2010/056424 also discloses catheters with pressure reducing elements, throttles, refrigerants (e.g., a cryogenic refrigerants, a non-cryogenic refrigerants, etc.), and distal tips (see FIGS. 43-44 of PCT/US2010/056424) used for cryogenic ablation.

In addition, the embodiments, features, systems, delivery devices, materials, methods and techniques described herein may, in certain embodiments, be applied to or used in connection with any one or more of the embodiments, features, systems, devices, materials, methods and techniques disclosed in the above-mentioned of PCT Application No. PCT/US2010/056424 (Publication No. WO 2011/060200) and U.S. application Ser. Nos. 12/463,304 (U.S. Publication No. 2009/0306644; 12/913,702 (U.S. Publication No. 2011/0152855); and 13/081,406. PCT Application No. PCT/US2010/056424 (Publication No. WO 2011/060200) and U.S. application Ser. Nos. 12/463,304 (U.S. Publication No. 2009/0306644; 12/913,702 (U.S. Publication No. 2011/0152855); and 13/081,406 are in the appendix and form part of this application.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating a subject, comprising:

positioning an energy delivery device in a passageway of a vessel in the subject such that a first energy emitting assembly of the energy delivery device is placed along a first outer side of a cartilaginous ring of the vessel, and a second energy emitting assembly of the energy delivery device is placed along a second outer side of the cartilaginous ring of the vessel; and delivering energy from the energy delivery device to nerve tissue in a target region along the vessel such that at least a portion of the nerve tissue is replaced by scar tissue which inhibits reinnervation in the target region.

2. The method of claim 1, further comprising inflating at least one of the first and second energy emitting assemblies against the vessel.

3. The method of claim 2, wherein the first and second energy emitting assemblies are respectively inflated with differing first and second fluids.

4. The method of claim 1, further comprising controlling first and second temperatures respectively of the first and second energy emitting assemblies.

5. The method of claim 4, wherein the first temperature differs from the second temperature.

6. The method of claim 4, further comprising circulating fluid through the first and second energy emitting assemblies.

7. The method of claim 1, wherein the first and second energy emitting assemblies respectively deliver differing first and second amounts of energy to the target region.

8. The method of claim 1, further comprising selecting the energy delivery device based on a width of the cartilaginous ring.

9. The method of claim 8, further comprising
inspecting the vessel with a delivery apparatus; and
inserting the energy delivery device through the delivery apparatus.

10. The method of claim 1, wherein one or more of the first and second energy emitting assemblies has multiple circumferentially spaced electrodes.

11. The method of claim 1, wherein the first and second energy emitting assemblies deliver energy simultaneously in a monopolar mode.

12. The method of claim 1, wherein the first and second energy emitting assemblies deliver energy sequentially in a monopolar mode.

13. The method of claim 1, further comprising placing an external electrode on a skin of the subject, wherein the first and second energy emitting assemblies deliver energy in a monopolar mode.

14. The method of claim 1, wherein the first and second energy emitting assemblies delivery energy in a bipolar mode.

15. A method to strategically damage a target region of nerve tissue along a vessel, comprising:
locating the target region with a delivery apparatus;
inserting an ablation assembly through the delivery apparatus to position a first portion of an energy emitting assembly of the ablation assembly along a first outer side of a cartilaginous ring of the vessel, and a second portion of the energy emitting assembly of the ablation assembly along a second outer side of the cartilaginous ring of the vessel; and
delivering energy from the energy emitting assembly into the target region.

16. The method of claim 15, wherein the first and second portions of the energy emitting assembly operate independently.

17. The method of claim 15, wherein the first and second portions of the energy emitting assembly comprise a first energy emitting assembly and a second energy emitting assembly, respectively, wherein the method further comprises
inflating the first energy emitting assembly with a first fluid at a first temperature; and
inflating the second energy emitting assembly with a second fluid at a second temperature, wherein the first temperature differs from the second temperature.

18. A method to ablate a target region of tissue along a vessel, comprising:
positioning an ablation assembly within the vessel to place first and second energy emitting assemblies respectively along first and second outer sides of a cartilaginous ring of the vessel proximate to the target region; and
energizing the first and second energy emitting assemblies.

19. The method of claim 18, wherein the first and second energy emitting assemblies operate independently.

* * * * *